United States Patent
Trubetskoy et al.

(10) Patent No.: US 7,098,032 B2
(45) Date of Patent: *Aug. 29, 2006

(54) COMPOSITIONS AND METHODS FOR DRUG DELIVERY USING PH SENSITIVE MOLECULES

(75) Inventors: Vladimir S. Trubetskoy, Madison, WI (US); James E. Hagstrom, Middleton, WI (US); Vladimir G. Budker, Middleton, WI (US); Jon A. Wolff, Madison, WI (US); David B. Rozema, Madison, WI (US); Sean D. Monahan, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/046,590

(22) Filed: Jan. 28, 2005

(65) Prior Publication Data

US 2005/0123600 A1 Jun. 9, 2005

Related U.S. Application Data

(63) Continuation of application No. 10/095,680, filed on Mar. 11, 2002, now Pat. No. 6,919,091, which is a continuation-in-part of application No. 09/753,990, filed on Jan. 2, 2001, now Pat. No. 6,383,811.

(51) Int. Cl.
*C12N 15/88* (2006.01)
(52) U.S. Cl. ............... 435/458; 424/450; 536/23.1
(58) Field of Classification Search ............... None
See application file for complete search history.

(56) References Cited

U.S. PATENT DOCUMENTS

| 6,881,516 B1 * | 4/2005 | Aamodt et al. ............. 429/181 |
| 2005/0170505 A1 * | 8/2005 | Wakefield et al. .......... 435/455 |

* cited by examiner

*Primary Examiner*—James Ketter
(74) *Attorney, Agent, or Firm*—Mark K. Johnson; Kirk Ekana

(57) ABSTRACT

An polyampholyte is utilized in a condensed polynucleotide complex for purposes of nucleic acid delivery to a cell. The complex can be formed with an appropriate amount of positive and/or negative charge such that the resulting complex can be delivered to the extravascular space and may be further delivered to a cell.

32 Claims, No Drawings

SEQUENCE LISTING

<160> NUMBER OF SEQ ID NOS: 10

<210> SEQ ID NO 1
<211> LENGTH: 13
<212> TYPE: PRT
<213> ORGANISM: Simian virus 40

<400> SEQUENCE: 1

Cys Gly Tyr Gly Pro Lys Lys Lys Arg Lys Val Gly Gly
1               5                   10

<210> SEQ ID NO 2
<211> LENGTH: 39
<212> TYPE: PRT
<213> ORGANISM: Simian virus 40

<400> SEQUENCE: 2

Cys Lys Lys Lys Ser Ser Ser Asp Glu Ala Thr Ala Asp Ser Gln
1               5                   10                  15

His Ser Thr Pro Pro Lys Lys Lys Arg Lys Val Glu Asp Pro Lys Asp
            20                  25                  30

Phe Pro Ser Glu Leu Leu Ser
        35

<210> SEQ ID NO 3
<211> LENGTH: 37
<212> TYPE: PRT
<213> ORGANISM: Simian virus 40

<400> SEQUENCE: 3

Cys Lys Lys Lys Trp Asp Asp Glu Ala Thr Ala Asp Ser Gln His Ser
1               5                   10                  15

```
Thr Pro Pro Lys Lys Arg Lys Val Glu Asp Pro Lys Asp Phe Pro
            20                  25                  30

Ser Glu Leu Leu Ser
            35

<210> SEQ ID NO 4
<211> LENGTH: 31
<212> TYPE: PRT
<213> ORGANISM: Homo sapiens

<400> SEQUENCE: 4

Cys Tyr Asn Asp Phe Gly Asn Tyr Asn Gln Ser Ser Asn Phe Gly
1               5                   10                  15

Pro Met Lys Gln Gly Asn Phe Gly Arg Ser Ser Gly Pro Tyr
            20                  25                  30

<210> SEQ ID NO 5
<211> LENGTH: 10
<212> TYPE: PRT
<213> ORGANISM: Human adenovirus type 5

<400> SEQUENCE: 5

Cys Lys Arg Gly Pro Lys Arg Pro Arg Pro
1               5                   10

<210> SEQ ID NO 6
<211> LENGTH: 22
<212> TYPE: PRT
<213> ORGANISM: Xenopus laevis

<400> SEQUENCE: 6

Cys Lys Lys Ala Val Lys Arg Pro Ala Ala Thr Lys Lys Ala Gly Gln
1               5                   10                  15

Ala Lys Lys Lys Lys Leu
            20

<210> SEQ ID NO 7
<211> LENGTH: 14
<212> TYPE: PRT
<213> ORGANISM: Homo sapiens

<400> SEQUENCE: 7

Cys Lys Lys Lys Gly Pro Ala Ala Lys Arg Val Lys Leu Asp
1               5                   10

<210> SEQ ID NO 8
<211> LENGTH: 21
<212> TYPE: PRT
<213> ORGANISM: Artificial
<220> FEATURE:
<223> OTHER INFORMATION: synthetic amphipathic peptide

<400> SEQUENCE: 8

Lys Leu Leu Lys Leu Leu Leu Lys Leu Trp Leu Lys Leu Leu Lys Leu
1               5                   10                  15

Leu Leu Lys Leu Leu
            20

<210> SEQ ID NO 9
<211> LENGTH: 26
<212> TYPE: PRT
<213> ORGANISM: Apis cerana

<400> SEQUENCE: 9
```

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20              25

<210> SEQ ID NO 10
<211> LENGTH: 8
<212> TYPE: PRT
<213> ORGANISM: Artificial
<220> FEATURE:
<223> OTHER INFORMATION: polyglutamate octomer

<400> SEQUENCE: 10

Glu Glu Glu Glu Glu Glu Glu Glu
1               5
```

COMPOSITIONS AND METHODS FOR DRUG DELIVERY USING PH SENSITIVE MOLECULES

CROSS-REFERENCE TO RELATED APPLICATIONS

This Application is a continuation of application Ser. No. 10/095,680, filed Mar. 11, 2002, now U.S. Pat. No. 6,919,091 which is a continuation-in-part of application Ser. No. 09/753,990 filed Jan. 2, 2001 now U.S. Pat. No. 6,383,811.

FIELD OF THE INVENTION

The invention relates to compounds and methods for use in biologic systems. More particularly, pH-sensitive polyampholytes are utilized for modifying the charge of particles, such as molecules, polymers, nucleic acids and genes for delivery to cells.

BACKGROUND OF THE INVENTION

Drug Delivery

A variety of methods and routes of administration have been developed to deliver pharmaceuticals that include small molecular drugs and biologically active compounds such as peptides, hormones, proteins, and enzymes to their site of action. Parenteral routes of administration include intravascular (intravenous, intraarterial), intramuscular, intraparenchymal, intradermal, subdermal, subcutaneous, intratumor, intraperitoneal, and intralymphatic injections that use a syringe and a needle or catheter. The blood circulatory system provides systemic spread of the pharmaceutical. Polyethylene glycol and other hydrophilic polymers have provided protection of the pharmaceutical in the blood stream by preventing its interaction with blood components and to increase the circulatory time of the pharmaceutical by preventing opsonization, phagocytosis and uptake by the reticuloendothelial system. For example, the enzyme adenosine deaminase has been covalently modified with polyethylene glycol to increase the circulatory time and persistence of this enzyme in the treatment of patients with adenosine deaminase deficiency.

The controlled release of pharmaceuticals after their administration is under intensive development. Pharmaceuticals have also been complexed with a variety of biologically-labile polymers to delay their release from depots. These polymers have included copolymers of poly(lactic/glycolic acid) (PLGA) (Jain, R. et al. Drug Dev. Ind. Pharm. 24, 703–727 (1998), ethylvinyl acetate/polyvinyl alcohol (Metrikin, D C and Anand, R, Curr Opin Ophthalmol 5, 21–29, 1994) as typical examples of biodegradable and non-degradable sustained release systems respectively.

Transdermal routes of administration have been effected by patches and ionotophoresis. Other epithelial routes include oral, nasal, respiratory, and vaginal routes of administration. These routes have attracted particular interest for the delivery of peptides, proteins, hormones, and cytokines, which are typically administered by parenteral routes using needles. For example, the delivery of insulin via respiratory, oral, or nasal routes would be very attractive for patients with diabetes mellitus. For oral routes, the acidity of the stomach (pH less than 2) is avoided for pH-sensitive compounds by concealing peptidase-sensitive polypaptides inside pH-sensitive hydrogel matrix (copolymers of polyethyleneglycol and polyacrylic acid). After passing low pH compartments of gastrointestinal tract such structures swells at higher pH releasing thus a bioactive compound (Lowman A M et al. J. Pharm. Sci. 88, 933–937 (1999). Capsules have also been developed that release their contents within the small intestine based upon pH-dependent solubility of a polymer. Copolymers of polymethacrylic acid (Eudragit S, Rohm America) are known as polymers which are insoluble at lower pH but readily solubilized at higher pH, so they are used as enteric coatings (Z Hu et al. J. Drug Target., 7, 223, 1999).

Biologically active molecules may be assisted by a reversible formation of covalent bonds. Quite often, it is found that the drug administered to a patient is not the active form of the drug, but is what is a called a prodrug that changes into the actual biologically active compound upon interactions with specific enzymes inside the body. In particular, anti-cancer drugs are quite toxic and are administered as prodrugs which do not become active until they come in contact with the cancerous cell (Sezaki, II., Takakura, Y., Hashida, M. Adv. Drug. Delivery Reviews 3, 193, 1989).

Recent studies have found that pH in solid tumors is 0.5 to 1 units lower than in normal tissue (Gerweck L E et al. Cancer Res. 56, 1194 (1996). Hence, the use of pH-sensitive polymers for tumor targeting is justified. However, this approach was demonstrated only in vitro (Berton, M, Eur. J. Pharm. Biopharm. 47, 119–23, 1999).

Liposomes were also used as drug delivery vehicles for low molecular weight drugs and macromolecules such as amphotericin B for systemic fungal infections and candidiasis. Inclusion of anti-cancer drugs such as adriamycin have been developed to increase their delivery to tumors and reduce it to other tissue sites (e.g. heart) thereby decreasing their toxicity. pH-sensitive polymers have been used in conjunction with liposomes for the triggered release of an encapsulated drug. For example, hydrophobically-modified N-isopropylacrylamide-methacrylic acid copolymer can render regular egg phosphatidyl chloline liposomes pH-sensitive by pH-dependent interaction of grafted aliphatic chains with lipid bilayer (O Meyer et al., FEBS Lett., 421, 61, 1998).

Gene and Nucleic Acid-Based Delivery

Gene or polynucleotide transfer is the cardinal process of gene therapy. The gene needs to be transferred across the cell membrane and enter the nucleus where the gene can be expressed. Gene transfer methods currently being explored included viral vectors and physical-chemical methods.

Viruses have evolved over millions of year to transfer their genes into mammalian cells. Viruses can be modified to carry a desired gene and become a "vector" for gene therapy. Using standard recombinant techniques, the harmful or superfluous viral genes can be removed and replaced with the desired normal gene. This was first accomplished with mouse retroviruses. The development of retroviral vectors were the catalyst that promoted current gene therapy efforts. However, they cannot infect all cell types very efficiently, especially in vivo. Other viral vectors based on Herpes virus are being developed to enable more efficient gene transfer into brain cells. Adenoviral and adenoassociated vectors are being developed to infect lung and other cells.

Besides using viral vectors, it is possible to directly transfer genes into mammalian cells. Usually, the desired gene is placed within bacterial plasmid DNA along with a mammalian promoter, enhancer, and other sequences that enable the gene to be expressed in mammalian cells. Several milligrams of the plasmid DNA containing all these sequences can be prepared and purified from the bacterial cultures. The plasmid DNA containing the desired gene can be incorporated into lipid vesicles (liposomes including cationic lipids such as Lipofectin) that then transfer the plasmid DNA into the target cell. Plasmid DNA can also be complexed with proteins that target the plasmid DNA to specific tissues just as certain proteins are taken up (endocytosed) by specific cells. Also, plasmid DNA can be complexed with polymers such as polylysine and polyethylenimine. Another plasmid-based technique involves "shooting" the plasmid DNA on small gold beads into the cell using a "gun". Finally, muscle cells in vivo have the unusual ability to take up and express plasmid DNA.

Gene therapy approaches can be classified into direct and indirect methods. Some of these gene transfer methods are most effective when directly injected into a tissue space. Direct methods using many of the above gene transfer techniques are being used to target tumors, muscle, liver, lung, and brain. Other methods are most effective when applied to cells or tissues that have been removed from the body and the genetically-modified cells are then transplanted back into the body. Indirect approaches in conjunction with retroviral vectors are being developed to transfer genes into bone marrow cells, lymphocytes, hepatocytes, myoblasts and skin cells.

Gene Therapy and Nucleic Acid-Based Therapies

Gene therapy promises to be a revolutionary advance in the treatment of disease. It is a fundamentally new approach for treating disease that is different from the conventional surgical and pharmaceutical therapies. Conceptually, gene therapy is a relatively simple approach. If someone has a defective gene, then gene therapy would fix the defective gene. The disease state would be modified by manipulating genes instead of their products, i.e. proteins, enzymes, enzyme substrates and enzyme products. Although, the initial motivation for gene therapy was the treatment of genetic disorders, it is becoming increasingly apparent that gene therapy will be useful for the treatment of a broad range of acquired diseases such as cancer, infectious disorders (AIDS), heart disease, arthritis, and neurodegenerative disorders (Parkinson's and Alzheimer's).

Gene therapy promises to take full-advantage of the major advances brought about by molecular biology. While, biochemistry is mainly concerned with how the cell obtains the energy and matter that is required for normal function, molecular biology is mainly concerned with how the cell gets the information to perform its functions. Molecular biology wants to discover the flow of information in the cell. Using the metaphor of computers, the cell is the hardware while the genes are the software. In this sense, the purpose of gene therapy is to provide the cell with a new program (genetic information) so as to reprogram a dysfunctional cell to perform a normal function. The addition of a new cellular function is provided by the insertion of a foreign gene that expresses a foreign protein or a native protein at amounts that are not present in the patient.

The inhibition of a cellular function is provided by anti-sense approaches (that is acting against messenger RNA) and that includes oligonucleotides complementary to the messenger RNA sequence and ribozymes. Messenger RNA (mRNA) is an intermediate in the expression of the DNA gene. The mRNA is translated into a protein. "Antisense" methods use an RNA sequence or an oligonucleotide that is made complementary to the target mRNA sequence and therefore binds specifically to the target messenger RNA. When this anti-sense sequence binds to the target mRNA, the mRNA is somehow destroyed or blocked from being translated. Ribozymes destroy a specific mRNA by a different mechanism. Ribozymes are RNA's that contain sequence complementary to the target messenger RNA plus a RNA sequence that acts as an enzyme to cleave the messenger RNA, thus destroying it and preventing it from being translated. When these anti-sense or ribozyme sequences are introduced into a cell, they would inactivate their specific target mRNA and reduce their disease-causing properties.

Gene therapy can be used as a type of vaccination to prevent infectious diseases and cancer. When a foreign gene is transferred into a cell and the protein is made, the foreign protein is presented to the immune system differently from simply injecting the foreign protein into the body. This different presentation is more likely to cause a cell-mediated immune response which is important for fighting latent viral infections such as human immunodeficiency virus (HIV causes AIDS), Herpes and cytomegalovirus. Expression of the viral gene within a cell simulates a viral infection and induces a more effective immune response by fooling the body that the cell is actually infected by the virus, without the danger of an actual viral infection.

Polymers for Drug and Nucleic Acid Delivery

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycation complexes. It has been shown that cationic proteins like histones and protamines or synthetic polymers like polylysine, polyarginine, polyomithine, DEAE dextran, polybrene, and polyethylenimine may be effective intracellular delivery agents while small polycations like spermine are ineffective. The following are some important principles involving the mechanism by which polycations facilitate uptake of DNA:

Polycations provide attachment of DNA to the cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a convenient linker for attaching specific ligands to DNA and as result, DNA-polycation complexes can be targeted to specific cell types.

Polycations protect DNA in complexes against nuclease degradation. This is important for both extra- and intracellular preservation of DNA. Gene expression is also enabled or increased by preventing endosome acidification with $NH_4Cl$ or chloroquine. Polyethylenimine, which facilitates gene expression without additional treatments, probably disrupts endosomal function itself. Disruption of endosomal function has also been accomplished by linking to the polycation endosomal-disruptive agents such as fusion peptides or adenoviruses.

Polycations can also facilitate DNA condensation. The volume which one DNA molecule occupies in a complex with polycations is drastically lower than the volume of a free DNA molecule. The size of a DNA/polymer complex is probably critical for gene delivery in vivo. In terms of intravenous injection, DNA needs to cross the endothelial barrier and reach the parenchymal cells of interest. The largest endothelia fenestrae (holes in the endothelial barrier)

occur in the liver and have an average diameter of 100 nm. The trans-epithelial pores in other organs are much smaller, for example, muscle endothelium can be described as a structure which has a large number of small pores with a radius of 4 nm, and a very low number of large pores with a radius of 20–30 nm. The size of the DNA complexes is also important for the cellular uptake process. After binding to the cells the DNA-polycation complex should be taken up by endocytosis. Since the endocytic vesicles have a homogenous internal diameter of about 100 nm in hepatocytes and are of similar size in other cell types, DNA complexes smaller than 100 nm are preferred.

Condensation of DNA

A significant number of multivalent cations with widely different molecular structures have been shown to induce condensation of DNA.

Two approaches for compacting (used herein as an equivalent to the term condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized.

2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect.

The mechanism of DNA condensation is not clear. The electrostatic force between unperturbed helices arises primarily from a counterion fluctuation mechanism requiring multivalent cations and plays a major role in DNA condensation. The hydration forces predominate over electrostatic forces when the DNA helices approach closer then a few water diameters. In a case of DNA-polymeric polycation interactions, DNA condensation is a more complicated process than the case of low molecular weight polycations. Different polycationic proteins can generate toroid and rod formation with different size DNA at a ratio of positive to negative charge of two to five. T4 DNA complexes with polyarginine or histone can form two types of structures; an elongated structure with a long axis length of about 350 nm (like free DNA) and dense spherical particles. Both forms exist simultaneously in the same solution. The reason for the co-existence of the two forms can be explained as an uneven distribution of the polycation chains among the DNA molecules. The uneven distribution generates two thermodynamically favorable conformations.

The electrophoretic mobility of DNA-polycation complexes can change from negative to positive in excess of polycation. It is likely that large polycations don't completely align along DNA but form polymer loops that interact with other DNA molecules. The rapid aggregation and strong intermolecular forces between different DNA molecules may prevent the slow adjustment between helices needed to form tightly packed orderly particles.

As previously stated, preparation of polycation-condensed DNA particles is of particular importance for gene therapy, more specifically, particle delivery such as the design of non-viral gene transfer vectors. Optimal transfection activity in vitro and in vivo can require an excess of polycation molecules. However, the presence of a large excess of polycations may be toxic to cells and tissues. Moreover, the non-specific binding of cationic particles to all cells forestalls cellular targeting. Positive charge also has an adverse influence on biodistribution of the complexes in vivo.

Several modifications of DNA-cation particles have been created to circumvent the nonspecific interactions of the DNA-cation particle and the toxicity of cationic particles. Examples of these modifications include attachment of steric stabilizers, e.g. polyethylene glycol, which inhibit nonspecific interactions between the cation and biological polyanions. Another example is recharging the DNA particle by the additions of polyanions which interact with the cationic particle, thereby lowering its surface charge, i.e. recharging of the DNA particle U.S. Ser. No. 09/328,975. Another example is cross-linking the polymers and thereby caging the complex U.S. Ser. No. 08/778,657, U.S. Ser. No. 09/000,692, U.S. Ser. No. 97/24089, U.S. Ser. No. 09/070,299, and U.S. Ser. No. 09/464,871. Nucleic acid particles can be formed by the formation of chemical bonds and template polymerization U.S. Ser. No. 08/778,657, U.S. Ser. No. 09/000,692, U.S. Ser. No. 97/24089, U.S. Ser. No. 09/070,299, and U.S. Ser. No 09/464,871.

A problem with these modifications is that they are most likely irreversible rendering the particle unable to interact with the cell to be transfected, and/or incapable of escaping from the lysosome once taken into a cell, and/or incapable of entering the nucleus once inside the cell. A method for formation of DNA particles that is reversible under conditions found in the cell may allow for effective delivery of DNA. The conditions that cause the reversal of particle formation may be, but not limited to, the pH, ionic strength, oxidative or reductive conditions or agents, or enzymatic activity.

DNA Template Polymerization

Low molecular weight cations with valency, i.e. charge, <+3 fail to condense DNA in aqueous solutions under normal conditions. However, cationic molecules with the charge <+3 can be polymerized in the presence of DNA and the resulting polymers can cause DNA to condense into compact structures. Such an approach is known in synthetic polymer chemistry as template polymerization. During this process, monomers (which are initially weakly associated with the template) are positioned along template's backbone, thereby promoting their polymerization. Weak electrostatic association of the nascent polymer and the template becomes stronger with chain growth of the polymer. Trubetskoy et al used two types of polymerization reactions to achieve DNA condensation: step polymerization and chain polymerization (VS Trubetskoy, V G Budker, L J Hanson, P M Slattum, J A Wolff, L E Hagstrom. Nucleic Acids Res. 26:4178–4185, 1998) U.S. Ser. No. 08/778,657, U.S. Ser. No. 09/000,692, U.S. Ser. No. 97/24089, U.S. Ser. No. 09/070,299, and U.S. Ser. No. 09/464,871. Bis(2-aminoethyl)-1,3-propanediamine (AEPD), a tetramine with 2.5 positive charges per molecule at pH 8 was polymerized in the presence of plasmid DNA using cleavable disulfide aminoreactive cross-linkers dithiobis (succinimidyl propionate) and dimethyl-3,3'-dithiobispropionimidate. Both reactions yielded DNA/polymer complexes with significant retardation in agarose electrophoresis gels demonstrating significant binding and DNA condensation. Treatment of the polymerized complexes with 100 mM dithiothreitol (DTT) resulted in the pDNA returning to its normal supercoiled position following electrophoresis proving thus cleavage the backbone of the. The template dependent polymerization process was also tested using a 14 mer peptide encoding the nuclear localizing signal (NLS) of SV40 T antigen (CGYG-PKKKRKVGGC SEQ ID 11), as a cationic "macromonomer". Other studies included pegylated comonomer (PEG-AEPD) into the reaction mixture and resulted in "worm"-like structures (as judged by transmission electron microscopy) that have previously been observed with DNA complexes formed from block co-polymers of polylysine and PEG (M A Wolfert, E H Schacht, V Toncheva, K Ulbrich, O Nazarova, L W Seymour. Human Gene Ther. 7:2123–2133, 1996). Blessing et al used bisthiol derivative of spermine and reaction of thiol-disulfide exchange to promote chain growth. The presence of DNA accelerated the polymerization reaction as measured the rate of disappearance of free thiols in the reaction mixture (T Blessing, J S Remy, J P Behr. J. Am. Chem. Soc. 120:8519–8520, 1998).

Caging of Polycation-Condensed DNA Particles.

The stability of DNA nanoassemblies based on DNA condensation is generally low in vivo because they easily engage in polyion exchange reactions with strong polyanions. The process of exchange consists of two stages: 1) rapid formation of a triple DNA-polycation-polyanion complex, 2) slow substitution of one same-charge polyion with another. At equilibrium conditions, the whole process eventually results in formation of a new binary complex and an excess of a third polyion. The presence of low molecular weight salt can greatly accelerate such exchange reactions, which often result in complete disassembly of condensed DNA particles. Hence, it is desirable to obtain more colloidally stable structures where DNA would stay in its condensed form in complex with corresponding polycation independently of environment conditions.

The complete DNA condensation upon neutralization of only 90% of the polymer's phosphates results in the presence of unpaired positive charges in the DNA particles. If the polycation contains such reactive groups, such as primary amines, these unpaired positive charges may be modified. This modification allows practically limitless possibilities of modulating colloidal properties of DNA particles via chemical modifications of the complex. We have demonstrated the utility of such reactions using traditional DNA-poly-L-lysine (DNA/PLL) system reacted with the cleavable cross-linking reagent dimethyl-3,3'-dithiobispropionimidate (DTBP) which reacts with primary amino groups with formation of amidines (V S Trubetskoy, A Loomis, P M Slattum, J E Hagstrom, V G Budker, J A Wolff. Bioconjugate Chem. 10:624–628, 1999) U.S. Ser. No. 08/778,657, U.S. Ser. No. 09/000,692, U.S. Ser. No. 09/070,299, and U.S. Ser. No. 09/464,871. Similar results were achieved with other polycations including poly(allylamine) and histone H1. The use of another bifucntional reagent, glutaraldehyde, has been described for stabilization of DNA complexes with cationic peptide CWK18 (R C Adam, K G Rice. J. Pharm. Sci. 739–746, 1999).

Recharging.

The caging approach described above could lead to more colloidally stable DNA assemblies. However, this approach may not change the particle surface charge. Caging with bifunctional reagents, which preserve positive charge of amino group, keeps the particle positive. However, negative surface charge would be more desirable for many practical applications, i.e. in vivo delivery. The phenomenon of surface recharging is well known in colloid chemistry and is described in great detail for lyophobic/lyophilic systems (for example, silver halide hydrosols). Addition of polyion to a suspension of latex particles with oppositely-charged surface leads to the permanent absorption of this polyion on the surface and, upon reaching appropriate stoichiometry, changing the surface charge to opposite one. This whole process is salt dependent with flocculation to occur upon reaching the neutralization point.

We have demonstrated that similar layering of polyelectrolytes can be achieved on the surface of DNA/polycation particles (V S Trubetskoy, A Loomis, J E Hagstrom, V G Budker, J A Wolff. Nucleic Acids Res. 27:3090–3095, 1999). The principal DNA-polycation (DNA/pC) complex used in this study was DNA/PLL (1:3 charge ratio) formed in low salt 25 mM HEPES buffer and recharged with increasing amounts of various polyanions. The DNA particles were characterized after addition of a third polyion component to a DNA/polycation complex using a new DNA condensation assay (V S Trubetskoy, P M Slattum, J E Hagstrom, J A Wolff, V G Budker. Anal. Biochem. 267:309–313, 1999) and static light scattering. It has been found that certain polyanions such as poly(methacrylic acid) and poly(aspartic acid) decondensed DNA in DNA/PLL complexes. Surprisingly, polyanions of lower charge density such as succinylated PLL and poly(glutamic acid), even when added in 20-fold charge excess to condensing polycation (PLL) did not decondense DNA in DNA/PLL (1:3) complexes. Further studies have found that displacement effects are salt-dependent. In addition, poly-L-glutamic acid but not the relatively weaker polyanion succinylated poly-L-lysine (SPLL) displaces DNA at higher sodium chloride concentrations. Measurement of $\zeta$-potential of DNA/PLL particles during titration with SPLL revealed the change of particle surface charge at approximately the charge equivalency point. Thus, it can be concluded that addition of low charge density polyanion to the cationic DNA/PLL particles results in particle surface charge reversal while maintaining condensed DNA core intact. Finally, DNA/polycation complexes can be both recharged and crosslinked or caged U.S. Ser. No. 08/778,657, U.S. Ser. No. 09/000,692, U.S. Ser. No. 97/24089, U.S. Ser. No. 09/070,299, and U.S. Ser. No. 09/464,871.

The Use of pH-Sensitive Lipids, Amphipathic Compounds, and Liposomes for Drug and Nucleic Acid Delivery.

Cationic liposomes may deliver DNA either directly across the plasma membrane or via the endosome compartment. Regardless of its exact entry point, much of the DNA within cationic liposomes does accumulate in the endosome compartment. Several approaches have been investigated to prevent loss of the foreign DNA in the endosomal compartment by protecting it from hydrolytic digestion within the endosomes or enabling its escape from endosomes into the cytoplasm. They include the use of acidotropic (lysomotrophic), weak amines such as chloroquine that presumably prevent DNA degradation by inhibiting endosomal acidification (Legendre, J. & Szoka, F. Delivery of plasmid DNA into mammalian cell lines using pH-sensitive liposomes: Comparison with cationic liposomes. *Pharmaceut. Res.* 9, 1235–1242 (1992)). Viral fusion peptides or whole virus have been included to disrupt endosomes or promote fusion of liposomes with endosomes, and facilitate release of DNA into the cytoplasm (Kamata, H., Yagisawa, H., Takahashi, S. & Hirata, H. Amphiphilic peptides enhance the efficiency of liposome-mediated DNA transfection. *Nucleic Acids Res.* 22, 536–537 (1994). Wagner, E., Curiel, D. & Cotten, M. Delivery of drugs, proteins and genes into cells using transferrin as a ligand for receptor-mediated endocytosis. *Advanced Drug Delivery Reviews* 14, 113–135 (1994)).

Knowledge of lipid phases and membrane fusion has been used to design potentially more versatile liposomes that exploit the endosomal acidification to promote fusion with endosomal membranes. Such an approach is best exemplified by anionic, pH-sensitive liposomes that have been designed to destabilize or fuse with the endosome membrane at acidic pH (Duzgunes, N., Straubinger, R. M., Baldwin, P. A. & Papahadjopoulos, D. *PH-sensitive liposomes*. (eds Wilschub, J. & Hoekstra, D.) p. 713–730 (Marcel Deker INC, 1991)). All of the anionic, pH-sensitive liposomes have utilized phosphatidylethanolamine (PE) bilayers that are stabilized at non-acidic pH by the addition of lipids that contain a carboxylic acid group. Liposomes containing only PE are prone to the inverted hexagonal phase ($H_{II}$). In pH-sensitive, anionic liposomes, the carboxylic acid's negative charge increases the size of the lipid head group at pH greater than the carboxylic acid's $pK_a$ and thereby stabilizes the phosphatidylethanolamine bilayer. At acidic pH conditions found within endosomes, the uncharged or reduced charge species is unable to stabilize the phosphatidylethanolamine-rich bilayer. Anionic, pH-sensitive liposomes have delivered a variety of membrane-impermeable compounds including DNA. However, the negative charge of these pH-sensitive liposomes prevents them from efficiently taking up DNA and interacting with cells; thus decreasing their utility for transfection. We have described the use of cationic, pH-sensitive liposomes to mediate the efficient transfer of DNA into a variety of cells in culture U.S. Ser. No. 08/530,598, and U.S. Ser. No. 09/020,566.

The Use of pH-Sensitive Polymers for Drug and Nucleic Acid Delivery

Polymers that pH-sensitive are have found broad application in the area of drug delivery exploiting various physiological and intracellular pH gradients for the purpose of controlled release of drugs (both low molecular weight and polymeric). pH sensitivity can be broadly defined as any change in polymer's physico-chemical properties over certain range of pH. More narrow definition demands significant changes in the polymer's ability to retain (release) a bioactive substance (drug) in a physiologically tolerated pH range (usually pH 5.5–8). All polyions can be divided into three categories based on their ability to donate or accept protons in aqueous solutions: polyacids, polybases and polyampholytes. Use of pH-sensitive polyacids in drug delivery applications usually relies on their ability to become soluble with the pH increase (acid/salt conversion), to form complex with other polymers over change of pH or undergo significant change in hydrophobicity/hydrophilicity balance. Combinations of all three above factors are also possible.

SUMMARY OF THE INVENTION

Described in a preferred embodiment is a process for enhancing delivery of a polyion to a cell, comprising the formation of a complex of a pH-labile polyampholyte and polyion. Then, delivering the complex into a cell.

DETAILED DESCRIPTION

The present invention relates to the delivery of desired compounds (e.g., drugs and nucleic acids) into cells using pH-labile polyampholytes and membrane active compounds coupled with labile compounds. The present invention provides compositions and methods for delivery and release of a compound of interest to a cell.

Polyampholytes are copolyelectrolytes containing both polycations and polyanions in the same polymer. In aqueous solutions polyampholytes are known to precipitate near the isoelectric point and form micelle-like structures (globules) at the excess of either charge. Such globules maintain tendency to bind other charged macromolecules and particles (see R R Netz, J F Joanny, Macromolecules, 31, 5123–5141 (1998)).

In provisional application Ser. No. 60/093,153 we described gene transfer activity which can be substantially increased by adding polyanions to preformed DNA/polycation complexes(i.e. recharging). We confirmed the same phenomenon for cationic lipids (provisional application Ser. No. 60/150,160). We extended this principle into situations where DNA-binding polycation and polyanion are covalently linked into one polymer. In this application we investigated the use of polyampholytes that contain pH-labile bonds.

It has previously been demonstrated that binding of negatively-charged serum components can significantly decrease gene transfer efficacy of DNA/polycation (DNA/pC) complexes in vivo (Vitiello L, Bockhold K, Joshi P B, Worton P B, Gene Therapy 5, 1306–13 (1998); Ross P C, Hui S W, Gene Therapy 6, 651–659 (1999). We have found that addition of polyanions to the point of near complex charge reversal drastically increases the efficacy of gene transfer mediated by DNA/Polycation (pC) complex upon i/v administration in mice (Provisional application Ser. No. 60/093,153). This improvement takes place due to protecting effect of the polyacid (pA) that decreases the charge of the complex, thereby inhibiting interactions with negatively charged serum components. We believe that gene transfer increase observed with DNA/polyampholyte complexes is based on the same phenomenon by decreasing the charge of the DNA-polycation complex.

Formation of Polyampholytes

Conceptually, there are several ways in which one may form polyampholytes: monovalent block polyampholytes, multivalent block polyampholytes, alternating copolyampholytes and random copolyampholytes. All of these ways of constructing polyampholytes are equivalent in that they result in the formation of a polyampholyte.

Monovalent block polyampholytes are polyampholytes in which one covalent bond connects a polycation to a polyanion. Cleavage of this bond results in the formation of a polycation and a polyanion. For each polyelectrolyte there may be more than one attached polyelectrolyte of opposite charge, but the attachment between polymers is through one covalent bond.

Multivalent block polyampholytes are polyampholytes in which more than one bond connects polycation to polyanion. Cleavage of these bonds results in a polycation and a polyanion. A name for the process of connecting preformed polycations and polyanions into a multivalent block polyampholyte is crosslinking. For each polyelectrolyte there may be more than one attached polyelectrolyte of opposite charge.

Alternating copolyampholytes are polyampholytes in which the cationic and anionic monomers repeat in a repeating alternating sequence. The monomers in these polyampholytes may, but need not be, polymers themselves. Cleavage of the bonds between monomers results in anions and cations or polyanions and polycations (if the monomers are polycations and polycations).

Random copolyampholytes are polyampholytes in which the cationic and anionic monomers repeat in a random fashion. The monomers in these polyampholytes may, but need not be, polymers themselves. Cleavage of the bonds between monomers results in anions and cations or polyanions and polycations (if the monomers are polycations and polycations).

The present invention is related to the formation of DNA/polyampholyte complexes in which the polyampholyte contains a labile bond. The cleavage of pH labile bonds under acidic environments may either facilitate endosome disruption and/or release of free DNA or other polyion of interest from the complex. To demonstrate the principle we synthesized polyampholytes formed by the reversible acylation of a membrane active polycation by a derivative of maleic anhydride.

Prior to the present invention, delivery systems suffered from slow reversibility -or irreversibility- and/or high toxicity. For example, many cationic polymers such as poly-L-lysine (PLL) and polyethylenimine (PEI) form positively charged condensed particles with DNA. In vitro, these particles are relatively good reagents, compared to DNA alone, for the transfer of DNA into cells. However, these particles are poor transfer reagents in vivo due to their toxicity and relatively stable interaction with DNA, which renders their complexation irreversible under physiological conditions. There are several barriers that these complexes must overcome for them to be efficient gene transfer reagents: stable enough to protect the DNA from nucleases and aid in delivery to, the cell, yet the DNA polycation complex must be disrupted—thereby allowing transcription to occur. Additionally, if the complex is taken into the cell through the process of endocytosis, the complex must escape the endosome before being taken into the lysosome and being digested.

To assist in the disruption of the DNA complexes, certain embodiments of the present invention provide synthesized polyampholytes that are cleaved in the acid conditions found in the endosome (i.e., pH 5–7). For example, the present invention provides for the cleavage or alteration of a labile chemical group once the complex is in the desired environment: cleavage of the polyampholyte backbone resulting in smaller polyions or cleavage of the link between the polyampholyte backbone and the ion resulting in an ion and a polyampholyte. In either case, the number of molecules in the endosome increases. This alteration may facilitate the release of the delivered compound into the cytoplasm. Although it is not necessary to understand the mechanism in order to use the present invention, and it is not intended that the present invention be so limited, one can contemplate a number of mechanisms by which the delivery is enhanced by the present invention. In some instances cleavage of the labile polyampholyte leads to release and enhanced delivery of the therapeutic agent (biologically active compound). Cleavage can also lead to enhanced membrane activity so that the pharmaceutical (biologically active compound) is more effectively delivered to the cell. This can occur in the environs of a tumor or inflamed tissue or within an acidic sub-cellular compartment. Cleavage can also cause an osmotic shock to the endosomes and disrupts the endosomes. If the polyampholyte backbone is hydrophobic it may interact with the membrane of the endosome. Either effect disrupts the endosome and thereby assists in release of delivered compound.

In some embodiments of the present invention, membrane active agents are complexed with the delivery system such that they are inactive and not membrane active within the complex but become active when released, following the chemical conversion of the labile group. The membrane active agents may be used to assist in the disruption of the endosome or other cellular compartment. They can also be used to enable selective delivery or toxicity to tumors or tissues that are acidic. Many membrane active agents such as the peptides melittin and pardaxin and various viral proteins and peptides are effective in allowing a disruption of cellular compartments such as endosomes to effect a release of its contents into a cell. However, these agents are toxic to cells both in vitro and in vivo due to the inherent nature of their membrane activity. To decrease the toxicity of these agents, the present invention provides techniques to complex or modify the agent in a way which blocks or inhibits the membrane activity of the agent but is reversible in nature so activity can be recovered when membrane activity is needed for transport of biologically active compound. The activities of these membrane active agents can be controlled in a number of different ways. For example, a modification of the agent may be made that can be cleaved off of the agent allowing the activity to return. The cleavage can occur during a natural process, such as the pH drop seen in endosomes or cleaved in the cytoplasm of cells where amounts of reducing agents become available. Cleavage of a blocking agent can occur by delivery of a cleaving agent to the blocked complex at a time when it would be most beneficial. Another exemplary method of blocking membrane active agents is to reversibly modify the agents' functional group with an activity blocking addition (defined as "Compounds or Chemical Moieties that Inhibit or Block the Membrane Activity of Another Compound or Chemical Moiety". When the blocking addition reaches an environment or an adjunct is added the reversible modification is reversed and the membrane active agent will regain activity.

In some embodiments the biologically active compound is reversibly modified, or complexed with, an interaction modifier such that the interactions between the biologically active molecule and its environs, that is its interactions with itself and other molecules, is altered when the interaction modifier is released. For example attachment of such non-ionic hydrophilic groups such as polyethylene glycol and polysaccharides (e.g. starch) may decrease self-association and interactions with other molecules such as serum compounds and cellular membranes, which may be necessary for transport of the biologically active molecule to the cell. However these molecules may inhibit cellular uptake and therefore, must be lost before cellular uptake can occur. Likewise, cell targeting ligands aid in transport to a cell but may not be necessary, and may inhibit, transport into a cell. In all of these cases, the reversible attachment of the interaction modifier, through a labile bond, would be beneficial.

The present invention provides for the transfer of polynucleotides, and other biologically active compounds into cells in culture (also known as "in vitro"). Compounds or kits for the transfection of cells in culture is commonly sold as "transfection reagents" or "transfection kits". The present invention also provides for the transfer of polynucleotides, and biologically active compounds into cells within tissues in situ and in vivo, and delivered intravasculary (U.S. patent application Ser. No. 08/571,536), intrarterially, intravenous, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thryoid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. Compounds for the transfection of cells in vivo in a whole organism can be sold as "in vivo transfection reagents" or "in vivo transfection kits" or as a pharmaceutical for gene therapy.

Polyampholytes with pH-Labile Bonds

The present invention provides a wide variety of polyampholytes with labile groups that find use in the delivery systems of the present invention. The labile groups are selected such that they undergo a chemical transformation (e.g., cleavage) when present in physiological conditions. The chemical transformation may be initiated by the addition of a compound to the cell or may occur spontaneously when introduced into intra-and/or extra-cellular environments (e.g., the lower pH conditions of an endosome or the extracellular space surrounding tumors). The conditions under which a labile group will undergo transformation can be controlled by altering the chemical constituents of the molecule containing the labile group. For example, addition of particular chemical moieties (e.g., electron acceptors or donors) near the labile group can effect the particular conditions (e.g., pH) under which chemical transformation will occur.

In certain embodiments, the present invention provides compound delivery systems composed of polyampholytes that contain pH-labile groups. The systems are relatively chemically stable until they are introduced into acidic conditions that render them unstable (labile). An aqueous solution is acidic when the concentration of protons ($H^+$) exceed the concentration of hydroxide ($OH^-$). Upon delivery to the desired location, the labile group undergoes an acid-catalyzed chemical transformation resulting in release of the delivered compound or a complex of the delivered compound. The pH-labile bond may either be in the main-chain or in the side chain. If the pH-labile bond occurs in the main chain, then cleavage of the labile bond results in a decrease in polyampholyte length. If the pH-labile bond occurs in the side chain, then cleavage of the labile bond results in loss of side chain atoms from the polymer.

In some preferred embodiments of the present invention, nucleic acids are delivered to cells by a polyampholyte complex containing a labile group, or groups, that undergoes chemical transformation when exposed to the low pH environment of an endosome. Such complexes provide improved nucleic acid delivery systems, as they provide for efficient delivery and low toxicity.

Definitions: To facilitate an understanding of the present invention, a number of terms and phrases are defined below:

Biologically active compound: A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. In this specification, the cellular production of, or inhibition of a material, such as a protein, caused by a human assisting a molecule to an in vivo cell is an example of a delivered biologically active compound. Pharmaceuticals, proteins, peptides, polypeptides, enzyme inhibitors, hormones, cytokines, antigens, viruses, oligonucleotides, enzymes and nucleic acids are examples of biologically active compounds.

Peptide and polypeptide refer to a series of amino acid residues, more than two, connected to one another by amide bonds between the beta or alpha-amino group and carboxyl group of contiguous amino acid residues. The amino acids may be naturally occurring or synthetic. Polypeptide includes proteins and peptides, modified proteins and peptides, and non-natural proteins and peptides. Enzymes are proteins evolved by the cells of living organisms for the specific function of catalyzing chemical reactions. A chemical reaction is defined as the formation or cleavage of covalent or ionic bonds. Bioactive compounds may be used interchangeably with biologically active compound for purposes of this application.

Delivery of Biologically active compound: The delivery of a biologically active compound is commonly known as "drug delivery". "Delivered" means that the biologically active compound becomes associated with the cell or organism. The compound can be in the circulatory system, intravessel, extracellular, on the membrane of the cell or inside the cytoplasm, nucleus, or other organelle of the cell.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, and bile ducts. The intravascular route includes delivery through the blood vessels such as an artery or a vein. An administration route involving the mucosal membranes is meant to include nasal, bronchial, inhalation into the lungs, or via the eyes. Other routes of administration include intraparenchymal into tissues such as muscle (intramuscular), liver, brain, and kidney. Transdermal routes of administration have been effected by patches and ionotophoresis. Other epithelial routes include oral, nasal, respiratory, and vaginal routes of administration.

Delivery System: Delivery system is the means by which a biologically active compound becomes delivered. That is all compounds, including the biologically active compound itself, that are required for delivery and all procedures required for delivery including the form (such volume and phase (solid, liquid, or gas)) and method of administration (such as but not limited to oral or subcutaneous methods of delivery).

Nucleic Acid: The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nuclei acid includes deoxyribonucleic acid (DNA) and ribonucleic acid (RNA).

The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethyl-aminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

DNA may be in the form of anti-sense, plasmid DNA, parts of a plasmid DNA, product of a polymerase chain reaction (PCR), vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups.

"Anti-sense" is a polynucleotide that interferes with the function of DNA and/or RNA. This may result in suppression of expression. Natural nucleic acids have a phosphate backbone, artificial nucleic acids may contain other types of backbones and bases. These include PNAs (peptide nucleic acids), phosphothionates, morpholino and other variants of the phosphate backbone of native nucleic acids. In addition, DNA and RNA may be single, double, triple, or quadruple stranded.

The term "recombinant DNA molecule" as used herein refers to a DNA molecule that is comprised of segments of DNA joined together by means of molecular biological techniques. "Expression cassette" refers to a natural or recombinantly produced polynucleotide molecule that is capable of expressing protein(s). A DNA expression cassette typically includes a promoter (allowing transcription initiation), and a sequence encoding one or more proteins. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by homologous recombination, gene conversion, or other yet to be described mechanisms.

Gene: The term "gene" refers to a nucleic acid (e.g., DNA) sequence that comprises coding sequences necessary for the production of a polypeptide or precursor (e.g.,— myosin heavy chain). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form.

Gene Expression: As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

Delivery of Nucleic Acids: The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The delivery of nucleic acid can lead to modification of the DNA sequence of the target cell.

The polynucleotides or genetic material being delivered are generally mixed with transfection reagents prior to delivery. The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has irreversibly integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA. The term "naked polynucleotides" indicates that the polynucleotides are not associated with a transfection reagent or other delivery vehicle that is required for the polynucleotide to be delivered to a cell.

A "transfection reagent" or "delivery vehicle" is a compound or compounds that bind(s) to or complex(es) with oligonucleotides, polynucleotides, or other desired compounds and mediates their entry into cells. Examples of transfection reagents include, but are not limited to, cationic liposomes and lipids, polyamines, calcium phosphate precipitates, histone proteins, polyethylenimine, and polylysine complexes (polyethylenimine and polylysine are both toxic).

Typically, when used for the delivery of nucleic acids, the transfection reagent has a net positive charge that binds to the polynucleotide's negative charge. For example, cationic liposomes or polylysine complexes have net positive charges that enable them to bind to DNA or RNA.

Enzyme: Enzyme is a protein that acts as a catalyst. That is a protein that increases the rate of a chemical reaction without itself undergoing any permanent chemical change. The chemical reactions that are catalyzed by an enzyme are termed enzymatic reactions and chemical reactions that are not are termed nonenzymatic reactions.

Half-life: The half-life of a chemical reaction is the time required for one half of a given material to undergo a chemical reaction.

Complex: Two molecules are combined, to form a complex through a process called complexation or complex formation, if the are in contact with one another through noncovalent interactions such as coordination bonds, electrostatic interactions, hydrogen bonding interactions, and hydrophobic interactions.

Modification: A molecule is modified, to form a modification through a process called modification, by a second molecule if the two become bonded through a covalent bond. That is, the two molecules form a covalent bond between an atom form one molecule and an atom from the second molecule resulting in the formation of a new single molecule. A chemical covalent bond is an interaction, bond, between two atoms in which there is a sharing of electron density.

Osmosis: Osmosis is the passage of a solvent through a semipermeable membrane, a membrane through which solvent can pass but not all solutes, separating two solutions of different concentrations. There is a tendency for the separated solutions to become the same concentration as the solvent passes from low concentration to high concentration. Osmosis will stop when the two solutions become equal in concentration or when pressure is applied to the solution containing higher concentration. When the higher concentrated solution is in a closed system, that is when system is of constant volume, there is a build up of pressure as the solvent passes from low to high concentration. This build up of pressure is called osmotic pressure.

Salt: A salt is any compound containing ionic bonds, that is bonds in which one or more electrons are transferred completely from one atom to another. Salts are ionic compounds that dissociate into cations and anions when dissolved in solution and thus increase the ionic strength of a solution.

Interpolyelectrolyte Complexes: An interpolyelectrolyte complex is a noncovalent interaction between polyelectrolytes of opposite charge.

Charge, Polarity, and Sign: The charge, polarity, or sign of a compound refers to whether or not a compound has lost one or more electrons (positive charge, polarity, or sign) or gained one or more electrons (negative charge, polarity, or sign).

Cell Targeting Signals: Cell targeting signal (or abbreviated as the Signal) is defined in this specification as a molecule that modifies a biologically active compounds such as drug or nucleic acid and can direct it to a cell location (such as tissue) or location in a cell (such as the nucleus) either in culture or in a whole organism. By modifying the cellular or tissue location of the foreign gene, the function of the biologically active compound can be enhanced.

The cell targeting signal can be a protein, peptide, lipid, steroid, sugar, carbohydrate, (non-expressing) polynucleic acid or synthetic compound. The cell targeting signal enhances cellular binding to receptors, cytoplasmic transport to the nucleus and nuclear entry or release from endosomes or other intracellular vesicles.

Nuclear localizing signals enhance the targeting of the pharmaceutical into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS (H-CGYGPKKKRKVGG-OH, SEQ ID 1) or long NLS's (H-CKKKSSSDDEATAD-SQHSTP-PKKKRKVEDPKDFPSELLS-OH, SEQ ID 2; and H-CKKKWDDEATADSQHSTPP-KKKRKVEDPKD-FPSELLS-OH, SEQ ID 3). Other NLS peptides have been derived from M9 protein (CYNDFGNYNNQSSNFGP-MKQGNFGGRSSGPY, SEQ ID 4), E1A (H-CKRGP-KRPRP-OH, SEQ ID 5), nucleoplasmin (H-CK-KAVKRPAATKKAGQAKKKKL-OH, SEQ ID 6), and c-myc (H-CKKKGPAAKRVKLD-OH, SEQ ID 7).

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence, SEQ ID 12), viral components such as influenza virus hemagglutinin subunit HA-2 peptides and other types of amphipathic peptides.

Cellular receptor signals are any signal that enhances the association of the biologically active compound with a cell. This can be accomplished by either increasing the binding of the compound to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

Interaction Modifiers: An interaction modifier changes the way that a molecule interacts with itself or other molecules, relative to molecule containing no interaction modifier. The result of this modification is that self-interactions or interactions with other molecules are either increased or decreased. For example cell targeting signals are interaction modifiers with change the interaction between a molecule and a cell or cellular component. Polyethylene glycol is an interaction modifier that decreases interactions between molecules and themselves and with other molecules.

Reporter or Marker Molecules: Reporter or marker molecules are compounds that can be easily detected. Typically they are fluorescent compounds such as fluorescein, rhodamine, Texas red, cy 5, cy 3 or dansyl compounds. They can be molecules that can be detected by infrared, ultraviolet or visible spectroscopy or by antibody interactions or by electron spin resonance. Biotin is another reporter molecule that can be detected by labeled avidin. Biotin could also be used to attach targeting groups.

Linkages: An attachment that provides a covalent bond or spacer between two other groups (chemical moieties). The linkage may be electronically neutral, or may bear a positive or negative charge. The chemical moieties can be hydrophilic or hydrophobic. Preferred spacer groups include, but are not limited to C1–C12 alkyl, C1–C12 alkenyl, C1–C12 alkynyl, C6–C18 aralkyl, C6–C18 aralkenyl, C6–C18 aralkynyl, ester, ether, ketone, alcohol, polyol, amide, amine, polyglycol, polyether, polyamine, thiol, thio ether, thioester, phosphorous containing, and heterocyclic. The linkage may or may not contain one or more labile bonds.

Bifunctional: Bifunctional molecules, commonly referred to as crosslinkers, are used to connect two molecules together, i.e. form a linkage between two molecules. Bifunctional molecules can contain homo or heterobifunctionality.

Labile Bond: A labile bond is a covalent bond that is capable of being selectively broken. That is, the labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. Labile also means cleavable.

Labile Linkage: A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

pH-Labile Linkages and Bonds: pH-labile refers to the selective breakage of a covalent bond under acidic conditions (pH<7). That is, the pH-labile bond may be broken under acidic conditions in the presence of other covalent bonds without their breakage. The term pH-labile includes both linkages and bonds that are pH-labile, very pH-labile, and extremely pH-labile.

Very pH-Labile Linkages and Bonds: A subset of pH-labile bonds is very pH-labile. For the purposes of the present invention, a bond is considered very pH-labile if the half-life for cleavage at pH 5 is less than 45 minutes.

Extremely pH-Labile Linkages and Bonds: A subset of pH-labile bonds is extremely pH-labile. For the purposes of the present invention, a bond is considered extremely pH-labile if the half-life for cleavage at pH 5 is less than 15 minutes.

Amphiphilic and Amphipathic Compounds: Amphipathic, or amphiphilic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Membrane Active or Membrane Disruptive Compound: Membrane active or membrane disruptive agents or compounds are compounds (typically a polymer, polyampholyte, peptide or protein) that are able alter the membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. An example of a membrane active agent in our examples is the peptide melittin, whose membrane activity is demonstrated by its ability to release heme from red blood cells (hemolysis). In addition, dimethylmaleamic-modified melittin(DM-Mel) reverts to melittin in the acidic environment of the endosome causes endosomal release as seen by the diffuse staining of fluorescein-labeled dextran in our endosomal release assay.

More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane. In addition, transport between liposomes, or cell membranes, may be accomplished by the fusion of the two membranes and thereby the mixing of the contents of the two membranes.

Membrane active peptides: Membrane active peptides are peptides that have membrane activity. There are many naturally occurring membrane active peptides such as cecropin (insects), magainin, CPF 1, PGLa, Bombinin BLP-1 (all three from amphibians), melittin (bees), seminalplasmin (bovine), indolicidin, bactenecin (both from bovine neutrophils), tachyplesin 1 (crabs), protegrin (porcine leukocytes), and defensins (from human, rabbit, bovine, fungi, and plants). Gramicidin A and gramicidin S (*bacillus brevis*), the lantibiotics such as nisin (*lactococcus lactis*), androctonin (scorpion), cardiotoxin I (cobra), caerin (frog *litoria splendida*), dermaseptin (frog). Viral peptides have also been shown to have membrane activity, examples include hemagglutinin subunit HA-2 (influenza virus), E1 (Semliki forest virus), F1 (Sendai and measles viruses), gp41 (HIV), gp32 (SIV), and vp1 (Rhino, polio, and coxsackie viruses). In addition synthetic peptides have also been shown to have membrane activity. Synthetic peptides that are rich in leucines and lysines (KL or $KL_n$ motif) have been shown to have membrane activity. In particular, the peptide $H_2N$-KLLKLLLKLWLKLLKLLLKLL-$CO_2$ (SEQ ID 8), termed $KL_3$, is membrane active.

Compounds or Chemical Groups (Moieties) that Inhibit or Block the Membrane Activity of Another Compound or Chemical Moiety: An interaction with a membrane active agent by modification or complexation (including covalent, ionic, hydrogen bonding, coordination, and van der Waals bonds) with another compound that causes a reduction, or cessation of the said agents membrane activity. Examples include the covalent modification of a membrane-active peptide by the covalent attachment of an inhibitory chemical group (moiety) to the membrane disruptive peptide. Another example includes the interpolyelectrolyte complexation of a membrane disruptive polyanion and inhibitory polycation.

Derivative: Derivative, or substructure, means the chemical structure of the compound and any compounds derived from that chemical structure from the replacement of one or more hydrogen atoms by any other atom or change in oxidation state. For example if the substructure is succinic anhydride, then methylsuccinic anhydride, 2,2-dimethylsuccinic anhydride, 3-oxabicyclo(3.1.0)hexane-2,4-dione, maleic anhydride, citriconic anhydride, and 2,3-dimethylmaleic anhydride have the same substructure, or are derivatives. In the same way, derivatives of maleic anhydride include: methyl maleic anhydride, citraconic anhydride, dimethyl maleic anhydride, and 2-propionic-3-methylmaleic anhydride.

Polymers: A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. The side chain of a polymer is composed of the atoms whose bonds are not required for propagation of polymer length. For example in poly-L-lysine, the β, γ, δ, and ε-carbons, and ε-nitrogen are not required for the propagation of the polymer and are therefore side chain atoms.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990). Template polymerization can be used to form polymers from daughter polymers.

Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields-[A-B]-

Or the other approach is to have two difunctional monomers.

A-A+B-B yields-[A-A-B-B]-

Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate, or alkylphosphate, arylhalides (difluoro-dinitrobenzene), anhydrides or acid halides, p-nitrophenyl esters, o-nitrophenyl pentachlorophenyl esters, or pentafluorophenyl esters. In other terms when function A is an amine then function B can be acylating or alkylating agent or amination.

If functional group A is a thiol, sulfhydryl, then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimide is used. Other additives may be utilized such as carbonyldiimidazole, dimethylaminopyridine, N-hydroxysuccinimide or alcohol using carbodiimide and dimethylaminopyridine.

If functional group A is a hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used.

If functional group A is an aldehyde or ketone then function B can be (but not restricted to) an hydrazine, hydrazide derivative, amine (to form a imine or iminium that may or may not be reduced by reducing agents such as NaCNBH$_3$) or hydroxyl compound to form a ketal or acetal.

Yet another approach is to have one difunctional monomer so that

A-A plus another agent yields-[A-A]-.

If function A is a thiol, sulfhydryl, group then it can be converted to disulfide bonds by oxidizing agents such as iodine (I$_2$) or NaIO$_4$ (sodium periodate), or oxygen (O$_2$). Function A can also be an amine that is converted to a thiol, sulfhydryl, group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, thiol, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methacrylamide groups can undergo chain reaction, which can be radical, anionic, or cationic. Chain polymerization can also be accomplished by cycle or ring opening polymerization. Several different types of free radical initiators could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrazine, heterocycles (like imidazole, pyridine, morpholine, pyrimidine, or pyrene. The amines could be pH-sensitive in that the pK$_a$ of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide.

Monomers can also be hydrophobic, hydrophilic or amphipathic. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Polyelectrolyte: A polyelectrolyte, or polyion, is a polymer possessing more than one charge, i.e. the polymer contains groups that have either gained or lost one or more electrons. A polyelectrolyte possessing net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polyelectrolyte containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyelectrolyte includes polycation, polyanion, zwitterionic polymers, and neutral polymers. The term zwitterionic refers to the product (salt) of the reaction between an acidic group and a basic group that are part of the same molecule.

Chelator: A chelator is a polydentate ligand, a molecule that can occupy more than one site in the coordination sphere of an ion, particularly a metal ion, primary amine, or single proton. Examples of chelators include crown ethers, cryptates, and non-cyclic polydentate molecules. A crown ether is a cyclic polyether containing (—X—(CR1–2)n)m units, where n=1–3 and m=3–8. The X and CR 1–2 moieties can be substituted, or at a different oxidation states. X can be oxygen, nitrogen, or sulfur, carbon, phosphorous or any combination thereof. R can be H, C, O, S, N, P. A subset of crown ethers described as a cryptate contain a second (—X—(CR1–2)n)z strand where z=3–8. The beginning X atom of the strand is an X atom in the (—X—(CR1–2)n)m unit, and the terminal CH2 of the new strand is bonded to a second X atom in the (—X—(CR1–2)n)m unit. Non-cyclic polydentate molecules containing (—X—(CR1–2)n)m unit(s), where n=1–4 and m=1–8. The X and CR1–2 moieties can be substituted, or at a different oxidation states. X can be oxygen, nitrogen, or sulfur, carbon, phosphorous or any combination thereof.

Polychelator: A polychelator is a polymer associated with a plurality of chelators by an ionic or covalent bond and can include a spacer. The polymer can be cationic, anionic, zwitterionic, neutral, or contain any combination of cationic, anionic, zwitterionic, or neutral groups with a net charge being cationic, anionic or neutral, and may contain steric stabilizers, peptides, proteins, signals, or amphipathic compound for the formation of micellar, reverse micellar, or unilamellar structures. Preferably the amphipathic compound can have a hydrophilic segment that is cationic, anionic, or zwitterionic, and can contain polymerizable groups, and a hydrophobic segment that can contain a polymerizable group.

Steric Stabilizer: A steric stabilizer is a long chain hydrophilic group that prevents aggregation of final polymer by sterically hindering particle to particle electrostatic interactions. Examples include: alkyl groups, PEG chains, polysaccharides, alkyl amines. Electrostatic interactions are the non-covalent association of two or more substances due to attractive forces between positive and negative charges.

Buffers: Buffers are made from a weak acid or weak base and their salts. Buffer solutions resist changes in pH when additional acid or base is added to the solution.

Biological, Chemical, or Biochemical reactions: Biological, chemical, or biochemical reactions involve the formation or cleavage of ionic and/or covalent bonds.

Reactive: A compound is reactive if it is capable of forming either an ionic or a covalent bond with another compound. The portions of reactive compounds that are capable of forming covalent bonds are referred to as reactive functional groups.

Lipid: Any of a diverse group of organic compounds that are insoluble in water, but soluble in organic solvents such as chloroform and benzene. Lipids contain both hydrophobic and hydrophilic sections. Lipids is meant to include complex lipids, simple lipids, and synthetic lipids.

Complex Lipids: Complex lipids are the esters of fatty acids and include glycerides (fats and oils), glycolipids, phospholipids, and waxes.

Simple Lipids: Simple lipids include steroids and terpenes.

Synthetic Lipids: Synthetic lipids includes amides prepared from fatty acids wherein the carboxylic acid has been converted to the amide, synthetic variants of complex lipids in which one or more oxygen atoms has been substituted by another heteroatom (such as Nitrogen or Sulfur), and derivatives of simple lipids in which additional hydrophilic groups have been chemically attached. Synthetic lipids may contain one or more labile groups.

Fats: Fats are glycerol esters of long-chain carboxylic acids. Hydrolysis of fats yields glycerol and a carboxylic acid—a fatty acid. Fatty acids may be saturated or unsaturated (contain one or more double bonds).

Oils: Oils are esters of carboxylic acids or are glycerides of fatty acids.

Glycolipids: Glycolipids are sugar containing lipids. The sugars are typically galactose, glucose or inositol.

Phospholipids: Phospolipids are lipids having both a phosphate group and one or more fatty acids (as esters of the fatty acid). The phosphate group may be bound to one or more additional organic groups.

Wax: Waxes are any of various solid or semisolid substances generally being esters of fatty acids.

Fatty Acids: Fatty acids are considered the hydrolysis product of lipids (fats, waxes, and phosphoglycerides).

Hydrophobic Groups: Hydrophobic groups indicate in qualitative terms that the chemical moiety is water-avoiding. Typically, such chemical groups are not water soluble, and tend not to form hydrogen bonds.

Hydrophilic Groups: Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxy amides, carboxylic acids, sulfurs, or hydroxyls.

Hydrocarbon: Hydrocarbon means containing carbon and hydrogen atoms; and halohydrocarbon means containing carbon, halogen (F, Cl, Br, I), and hydrogen atoms.

Alkyl, alkene, alkyne, aryl: Alkyl means any $sp^3$-hybridized carbon-containing group; alkenyl means containing two or more $sp^2$ hybridized carbon atoms; aklkynyl means containing two or more sp hybridized carbon atoms; aralkyl means containing one or more aromatic ring(s) in addition containing $sp^3$ hybridized carbon atoms; aralkenyl means containing one or more aromatic ring(s) in addition to containing two or more $sp^2$ hybridized carbon atoms; aralkynyl means containing one or more aromatic ring(s) in addition to containing two or more sp hybridized carbon atoms; steroid includes natural and unnatural steroids and steroid derivatives.

Steroid: A steroid derivative means a sterol, a sterol in which the hydroxyl moiety has been modified (for example, acylated), or a steroid hormone, or an analog thereof. The modification can include spacer groups, linkers, or reactive groups.

Carbohydrate: Carbohydrates include natural and unnatural sugars (for example glucose), and sugar derivatives (a sugar derivative means a system in which one or more of the hydroxyl groups on the sugar moiety has been modified (for example, but not limited to, acylated), or a system in which one or more of the hydroxyl groups is not present).

Polyoxyethylene: Polyoxyethylene means a polymer having ethylene oxide units ($-(CH_2CH_2O)_n-$, where $n=2-3000$).

Compound: A compound is a material made up of two or more elements.

Electron Withdrawing and Donating Groups: Electron withdrawing group is any chemical group or atom composed of electronegative atom(s), that is atoms that tend to attract electrons. Electron donating group is any chemical group or atom composed of electropositive atom(s), that is atoms that tend to attract electrons.

Resonance Stabilization: Resonance stabilization is the ability to distribute charge on multiple atoms through pi bonds. The inductive effective, in a molecule, is a shift of electron density due to the polarization of a bond by a nearby electronegative or electropositive atom.

Sterics: Steric hindrance, or sterics, is the prevention or retardation of a chemical reaction because of neighboring groups on the same molecule.

Activated Carboxylate: An activated carboxylate is a carboxylic acid derivative that reacts with nucleophiles to form a new covalent bond. Nucleophiles include nitrogen, oxygen and sulfur-containing compounds to produce ureas, amides, carbonates, carbamates, esters, and thioesters. The carboxylic acid may be activated by various agents including carbodiimides, carbonates, phosphoniums, and uroniums to produce activated carboxylates acyl ureas, acylphosphonates, acid anhydrides, and carbonates. Activation of carboxylic acid may be used in conjunction with hydroxy and amine-containing compounds to produce activated carboxylates N-hydroxy-succinimide esters, hydroxybenzotriazole esters, N-hydroxy-5-norbornene-endo-2,3-dicarboximide esters, p-nitrophenyl esters, pentafluorophenyl esters, 4-dimethylaminopyridinium amides, and acyl imidazoles.

Nucleophile: A nucleophile is a species possessing one or more electron-rich sites, such as an unshared pair of electrons, the negative end of a polar bond, or pi electrons.

Cleavage and Bond Breakage: Cleavage, or bond breakage is the loss of a covalent bond between two atoms. Cleavable means that a bond is capable of being cleaved.

Substituted Group or Substitution: A substituted group or a substitution refers to chemical group that is placed onto a parent system instead of a hydrogen atom. For the compound methylbenzene (toluene), the methyl group is a substituted group, or substitution on the parent system benzene. The methyl groups on 2,3-dimethylmaleic anhydride are substituted groups, or substitutions on the parent compound (or system) maleic anhydride.

Primary and Secondary Amine: A primary amine is a nitrogen-containing compound that is derived by monosubstitution of ammonia ($NH_3$) by a carbon-containing group. A primary amine is a nitrogen-containing compound that is derived by disubstitution of ammonia ($NH_3$) by a carbon-containing group.

Pharmaceutically Acceptable Salt: Pharmaceutically acceptable salt means both acid and base addition salts.

Pharmaceutically Acceptable Acid Addition Salt: A pharmaceutically acceptable acid addition salt is those salts which retain the biological effectiveness and properties of the free bases, and are not biologically or otherwise undesirable, and which are formed with inorganic acids such as hydrochloric acid, hydrobromic acis, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethansulfonic acid, p=toluenesulfonic acid, salicylic acid, trifluoroacetic acid, and the like.

Pharmaceutically Acceptable Base Addition Salt: A pharmaceutically acceptable base addition salt is those salts which retain the biological effectiveness and properties of the free acids, and are not biologically or otherwise undesirable. The salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

Preferred Embodiments

The following description provides exemplary embodiments of the systems, compositions, and methods of the present invention. These embodiments include a variety of systems that have been demonstrated as effective delivery systems both in vitro and in vivo. The invention is not limited to these particular embodiments. The following topics are discussed in turn: I) Labile and pH-labile II) Polyampholytes containing labile bonds I. Labile and pH-Labile Bonds A) Labile bonds: In one embodiment, disulfide bonds are used in a variety of molecules, and polymers that include peptides, lipids, liposomes.

B) pH-labile bonds: In one embodiment, ketals that are labile in acidic environments (pH less than 7, greater than 4) to form a diol and a ketone are used in a variety of molecules and polymers that include peptides, lipids, and liposomes.

In one embodiment, acetals that are labile in acidic environments (pH less than 7, greater than 4) to form a diol and an aldehyde are used in a variety of molecules and polymers that include peptides, lipids, and liposomes.

In one embodiment, imines or iminiums that are labile in acidic environments (pH less than 7, greater than 4) to form an amine and an aldehyde or a ketone are used in a variety of molecules and polymers that include peptides, lipids, and liposomes.

The present invention additionally provides for the use of polymers containing silicon-oxygen-carbon linkages (either in the main chain of the polymer or in a side chain of the polymer) that are labile under acidic conditions. Organosilanes have long been utilized as oxygen protecting groups in organic synthesis due to both the ease in preparation (of the silicon-oxygen-carbon linkage) and the facile removal of the protecting group under acidic conditions. For example, silyl ethers and silylenolethers, both posses such a linkage. Silicon-oxygen-carbon linkages are susceptible to hydrolysis under acidic conditions forming silanols and an alcohol (or enol). The substitution on both the silicon atom and the alcohol carbon can affect the rate of hydrolysis due to steric and electronic effects. This allows for the possibility of tuning the rate of hydrolysis of the silicon-oxygen-carbon linkage by changing the substitution on either the organosilane, the alcohol, or both the organosilane and alcohol to facilitate the desired affect. In addition, charged or reactive groups, such as amines or carboxylate, may be linked to the silicon atom, which confers the labile compound with charge and/or reactivity.

The present invention additionally provides for the use of polymers containing silicon-nitrogen (silazanes) linkages (either in the main chain of the polymer or in a side chain of the polymer) that are susceptible to hydrolysis. Hydrolysis of a silazane leads to the formation of a silanol and an amine. Silazanes are inherently more susceptible to hydrolysis than is the silicon-oxygen-carbon linkage, however, the rate of hydrolysis is increased under acidic conditions. The substitution on both the silicon atom and the amine can affect the rate of hydrolysis due to steric and electronic effects. This allows for the possibility of tuning the rate of hydrolysis of the silazane by changing the substitution on either the silicon or the amine to facilitate the desired affect.

The present invention additionally provides for the use of polymers containing silicon-carbon linkages (either in the main chain of the polymer or in a side chain of the polymer) that are susceptible to hydrolysis. For example, arylsilanes, vinylsilanes, and allylsilanes all posses a carbon-silicon bond that is susceptible to hydrolysis.

To construct labile molecules, one may construct the molecule with bonds that are inherently labile such as disulfide bonds, diols, diazo bonds, ester bonds, sulfone bonds, acetals, ketals, enol ethers, enol esters, imines, imminiums, and enamines. In addition, one may construct a polymer in such a way as to put reactive groups, i.e. electrophiles and nucleophiles, in close proximity so that reaction between the function groups is more rapid than if the reactive groups are not in close proximity. Examples include having carboxylic acid derivatives (acids, esters, amides) and alcohols, thiols, carboxylic acids or amines in the same molecule reacting together to make esters, thiol esters, acid anhydrides or amides.

An example of the construction of labile molecules containing labile bonds is the use of the acid labile enol ether bond. The enol ether is an ether, a molecule containing a —C—O—C— linkage, in which one of the carbons bonded to oxygen is $sp^2$ hybridized and bonded to another carbon, i.e. an enol. Enols are unstable and rapidly convert to the carbonyl, i.e. the ketone or aldehyde. Enol ethers are stable, relative to enols, but under acidic aqueous conditions convert to alcohol and ketone or aldehyde. Depending on the structures of the carbonyl compound formed and the alcohol release, enol hydrolysis can be very pH-labile. In general, hydrolysis to form ketones is much faster than the rate of conversion to aldehydes. For example the rate of hydrolysis of ethyl isopropenyl ether to form ethanol and acetone is ca. 3600 times faster than the hydrolysis of ethyl trans-propenyl ether to form ethanol and propanal.

An illustrative embodiment of the present invention, in which proximity of reactive groups confers lability, is shown by the conversion of amine to amides with anhydrides. Reaction of an amine with an anhydride results in the formation of an amide and a carboxylic acid. As is the case with all chemical reactions, this coupling of amine and anhydride is, in theory, reversible. However, as is the case for many chemical reactions, the reverse reaction (between a carboxylic acid and amide to form an anhydride and amine) is so unfavorable that the reaction between an amine and an anhydride is considered irreversible. Exceptions to this irreversibility are observed when the anhydride is a cyclic anhydride such that the formed amide and acid are in the same molecule, an amide acid. Placement of both reactive groups (amide and carboxylic acid) in the same molecule accelerates their reaction such that amine-anhydride reactivity becomes functionally reversible. For example, the amide-acid product of succinic anhydride and a primary amine cleaves back to amine and anhydride 10,000 times faster than the products between noncyclic anhydride and a primary amine. In particular, the product of primary amines with maleic anhydride and maleic anhydride derivatives, maleamic acids, revert back to amine and anhydride with amazing speed, $1\times10^9$ to $1\times10^{13}$ times faster than its noncyclic analogues (Kirby, A J. *J. Adv. Phys. Org Chem.* 1980, 17, 183). Maleamic acids are the product of the reaction between an amine and maleic anhydride and its derivatives such as methyl maleic anhydride, dimethyl maleic anhydride and 2-propionic-3-methylmaleic anhydride.

The amide acid that converts to amine and anhydride is the protonated acid, not the deprotonated carboxylate. For this reason, cleavage of the amide acid to form amine and anhydride is pH-dependent. This pH-dependent reactivity can be exploited to form reversible pH-sensitive linkers. Linkers, or spacer molecules, are used to conjugate passenger molecules and carrier molecules, which increase the transport and delivery of passenger molecules. Specifically, cis-aconitic acid is used as such a pH-sensitive linker molecule. The γ-carboxylate is first coupled to a carrier molecule, a molecule that assists in delivery such as an interaction modifier or a targeting ligand. In a second step, either the α or β carboxylate is coupled to a passenger molecule, such as a biologically active compound, to form a pH-sensitive coupling of passenger and carrier molecules. An estimation of the kinetics of cleavage between passenger and carrier reveals that at pH 5 the half-life of cleavage is between 8 and 24 hours (Blattler, W. A.; Kuenzi, B. S.; Lambert, J. M.; Senter, P. D. *Biochemistry*, 1985, 24, 1517–1524).

The pH at which cleavage occurs is controlled by the addition of chemical constituents to the labile moiety. The rate of conversion of maleamic acids to amines and maleic anhydrides is strongly dependent on substitution ($R_2$ and $R_3$) of the maleic anhydride system. When $R_2$ is methyl (from citraconic anhydride and similar in substitution to cis-aconitic anhydride) the rate of conversion is 50-fold higher than when $R_2$ and $R_3$ are hydrogen (derived from maleic anhydride). When there are alkyl substitutions at both $R_2$ and $R_3$, disubstituted maleamic acids, (e.g., 2,3-dimethylmaleicanhydride) the rate increase is dramatic, 10000-fold faster than maleic anhydride. Indeed, modification of the polycation poly-L-lysine with 2,3-dimethylmaleic anhydride to form the polyanionic 2,3-dimethylmaleamic poly-L-lysine, followed by incubation at acidic pH resulted in loss of 2,3-dimethylmaleic and return of the polycation poly-L-lysine.

The half-life of this conversion was between 4 and 10 minutes at pH 5. This shows that conversion of 2,3-dimethylmaleamic acids (derived from the reaction between 2,3-dimethylmaleic anhydride and amines at basic pH), to amines and 2,3-dimethylmaleic anhydride at acidic pH is extremely labile. It is postulated that this increase in rate for 2,3-dimethylmaleamic acids is due to the steric interactions between the two methyl groups which increases the interaction between amide and carboxylate and thereby increases the rate of conversion to amine and anhydride. Therefore, it is anticipated that if $R_2$ and R3 are groups larger than hydrogen, which includes any conceivable group, the rate of amide-acid conversion to amine and anhydride will be faster than if $R_2$ and/or $R_3$ are hydrogen. One would expect that 2,3-diethylmaleamic acids to cleave faster than ethylmaleamic acids and so forth. In addition, we synthesized 2-propionic-3-methylmaleic anhydride ($R_2$=$CH_2CH_2COOH$ and $R_3$=$CH_3$) and found that the rate of 2-propionic-3-methylmaleamic acid cleavage was the same as that for 2,3-dimethylmaleamic acids.

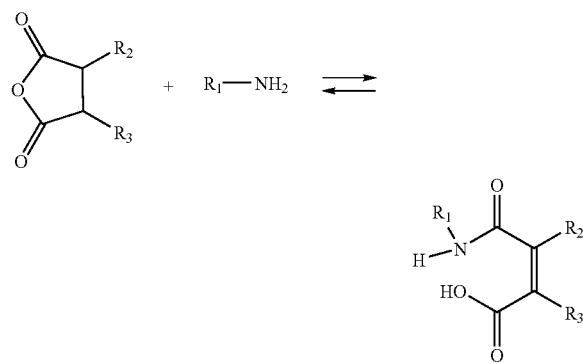

Reaction and reverse reaction of maleic anhydride derivatives with amines.

Another method for the production of rapidly cleaved pH-sensitive derivatives of maleic anhydride is to react the anhydride with an alcohol or thiol to form an acid ester or acid thioester.

II. Polyampholytes with pH-Labile Bonds

The present invention provides a wide variety of polyampholytes with labile groups that find use in the delivery systems of the present invention. The labile groups are selected such that they undergo a chemical transformation (e.g., cleavage) in physiological conditions, that is, when introduced into a specific, inherent intra or extracellular environment (e.g., the lower pH conditions of an endosome, or the extracellular environment of a cancerous tumor). In addition, the chemical transformation may also be initiated by the addition of a compound. The conditions under which a labile group will undergo transformation can be controlled by altering the chemical constituents of the molecule containing the labile group. For example, addition of particular chemical moieties (e.g., electron acceptors or donors) near the labile group can effect the particular conditions (e.g., pH) under which chemical transformation will occur. The present invention provides assays for the selection of the desired properties of the labile group for any desired application. A labile group is selected based upon its half-life and is included in a polyampholyte. The polyampholyte is then complexed with the biologically active compounds and an in vitro or in vivo assay is used to determine whether the compound's activity is affected.

A polyampholyte containing labile bonds may be either constructed by having labile bonds in the side chains of the monomers or in the main chain of the polyampholytes. In addition, block polyampholytes may be constructed by linking polycations and polyanions by labile bonds In some preferred embodiments of the present invention, the labile polyampholyte becomes more membrane disruptive upon cleavage of the labile group. Examples include, the reversible acylation of the peptide melittin (GIGAVLKVLTTGLPALISWIKRKRQQ, SEQ ID 9) by derivatives of maleic anhydride. Upon reaction with anhydride, the melittin becomes a negatively-charged polyampholyte containing two positive charges from the unreactive arginine groups. When the maleamate groups cleave under acidic conditions, the melittin becomes cationic and much more membrane disruptive. In the same way, other membrane active polycations can also be reversibly modified to become labile polyampholytes. Examples of membrane active polycations include peptides such as cecropin, magainin, CPF 1, PGLa, Bombinin BLP-1, seminalplasmin, indolicidin, bactenecin (both from bovine neutrophils), tachyplesin 1, protegrin, and defensins. Synthetic examples of membrane active polycations include polycations containing alkyl groups such as amine-containing enol ether copolymers, aklylated polycations, and acylated polycations.

A. pH-Labile Linkages Within pH-Labile Polyampholytes

The pH-labile bond may either be in the main-chain or in the side chain of the polyampholyte's constituent monomers. If the pH-labile bond occurs in the main chain, then cleavage of the labile bond results in a decrease in polyampholyte length. If the pH-labile bond occurs in the side chain, then cleavage of the labile bond results in loss of side chain atoms from the polyampholyte. For block polyampholytes, the labile bond may connect the polyanion(s) and polycation(s).

An example of a pH-labile bond in the side chain of a polyampholyte is partially 2,3-dimethylmaleamylated poly-L-lysine, which is a random copolyamphiphile. This polyampholyte is formed by the reaction of poly-L-lysine with less than one equivalent of 2,3-dimethylmaleic anhydride under basic conditions. The modification of the poly-L-lysine is in the side chain and conversion of the 2,3-dimethylmaleamic side chain to poly-L-lysine and 2,3-dimethylmaleic anhydride under acid conditions does not result in a cleavage of the polymer main, but in a cleavage of the side chain.

Labile block polyampholytes may be constructed by labile bonds in the constituent polyelectrolytes and/or the bond between the constituent polyelectrolytes. An example of a labile block polyampholyte composed of a labile constituent polyanion is fully maleamylated PLL that has been reacted with a mixture of 2-propionic-3-methylmaleic anhydride and a thioester derivative of 2-propionic-3-methylmaleic anhydride. The thioester provides an activated ester that reacts amines of cysteine groups. Addition of this labile polyanion to a cysteine-containing polycation results in the formation of a multivalent block polyampholyte.

A labile bond between a labile polyanion and a polycation may be made by formation of a labile polyanion by reaction of PLL with a mixture of 2-propionic-3-methylmaleic anhydride and an aldehyde derivative of 2-propionic-3-methylmaleic anhydride. The aldehyde is able to form an imine bond with an amine. Addition of this labile polyanion to a polyamine results in the formation of a multivalent block polyampholyte in which the connection between polycation and polyanion is labile.

B. Types of Monomers for Incorporation Into pH-Labile Polyampholytes and Types of pH-Labile Polymers A wide variety of monomers can be used in the polymerization processes. These include positive charged organic monomers such as amines, amine salts, imidine, guanidine, imine, hydroxylamine, hydrazine, heterocycles like imidazole, pyridine, morpholine, pyrimidine, or pyrene. Polymers from such monomers includes, but are not limited to such examples as poly-L-lysine, polyethylenimine (linear and branched), and polyallylamine The amines could be pH-sensitive in that the pKa of the amine is within the physiologic range of 4 to 8. Specific pH-sensitive amines include spermine, spermidine, N,N'-bis(2-aminoethyl)-1,3-propanediamine (AEPD), and 3,3'-Diamino-N,N-dimethyldipropylammonium bromide.

In addition negatively charged monomers such as sulfates, sulfonates, carboxylates, and phosphates may be used to generated polyanionic polymers. Examples of these polyanions include, but are not limited to, nucleic acids, polysulfonylstyrene, and heparin sulfate. Also, amine-containing polycations may be converted to polyanions by reaction with cyclic anhydrides such as succinic anhydride and glutaric anhydride to form glutarylated and succinylated polymers which are polyanionic. Examples of these polyanions include, but are not limited to, succinylated and glutarylated poly-L-lysine, and succinylated and glutarylated polyallylamine.

Monomers can also be hydrophobic, hydrophilic or amphipathic.

Monomers can also be intercalating agents such as acridine, thiazole organge, or ethidium bromide. Monomers can also contain chemical moieties that can be modified before or after the polymerization including (but not limited to) amines (primary, secondary, and tertiary), amides, carboxylic acid, ester, hydroxyl, hydrazine, alkyl halide, aldehyde, and ketone.

The pH-labile polyampholyte can also contain a chelator and be a polychelator.

C. Other Components of the Monomers and Polymers

The polyampholytes may include other groups that increase their utility. These groups can be incorporated into monomers prior to polymer formation or attached to the polymer after its formation. These groups include, but are not limited to: targeting groups and signals (e.g, cell receptor, nuclear targeting signals), membrane active compounds, reporter or marker molecules, spacers, steric stabilizers, chelators, polycations, polyanions, and polymers.

In one preferred embodiment, polycations are selected from the group including but not limited to poly-L-lysine, poly-D-lysine, poly-L,D-lysine, polyethylenimine (linear and/or branched), polyallylamine, poly-L-ornithine, poly-D-ornithine, poly-L,D-ornithine, polyvinylamine, natural cationic proteins, synthetic cationic proteins, synthetic cationic peptides and synthetic polymers containing monomers with amines selected from but not limited to alkylamine, aryl amine, aralkylamine, imidazole, pyridine, and piperazine, pyrazine, pyrimidine, oxazoline, oxazole, oxazolidine.

In another preferred embodiment, polyanions are selected from the group including but not limited to poly-L-aspartic acid, poly-D-aspartic acid, poly-L,D-aspartic acid, polyacrylic acid, poly-L-glutamic acid, poly-D-glutamic acid, poly-L,D-glutamic acid, succinylated poly-L-lysine, succinylated poly-D-lysine, succinylated poly-L,D-lysine, succinylated polyethyleneimine, succinylated polyallylamine, succinylated poly-L-ornithine, succinylated poly-D-ornithine, succinylated poly-L,D-ornithine, succinylated polyvinylamine, polymethacrylic acid, dextran sulfate, heparin, hyaluronic acid, DNA, RNA, natural anionic proteins, synthetic anionic proteins, synthetic anionic peptides, and synthetic polymers continuing monomers in which an amine has been reacted with a substructure of succinic anhydride.

In another preferred imbodiement, pH labile bonds include, but are not limited to acetal, ketal, silyl ether, silazane, imine, derivatives of citriconic anhydride, derivatives of maleic anhydride, derivatives of a crown ether (or azacrown ether, or thiacrown ether).

EXAMPLES

Example 1

Synthesis of Compounds Utilized in the Formation of Polyampholytes.

A) Synthesis of 2-propionic-3-methylmaleic anhydride (carboxydimethylmaleic anhydride or C-DM). To a suspension of sodium hydride (0.58 g, 25 mmol) in 50 mL anhydrous tetrahydrofuran was added triethyl-2-phosphonopropionate (7.1 g, 30 mmol). After bubbling of hydrogen gas stopped, dimethyl-2-oxoglutarate (3.5 g, 20 mmol) in 10 mL anhydrous tetrahydrofuran was added and stirred for 30 minutes. Water, 10 mL, was then added and the tetrahydrofuran was removed by rotary evaporation. The resulting solid and water mixture was extracted with 3×50 mL ethyl ether. The ether extractions were combined, dried with magnesium sulfate, and concentrated to a light yellow oil. The oil was purified by silica gel chromatography elution with 2:1 ether:hexane to yield 4 gm (82% yield) of pure triester. The 2-propionic-3-methylmaleic anhydride then formed by dissolving of this triester into 50 mL of a 50/50 mixture of water and ethanol containing 4.5 g (5 equivalents) of potassium hydroxide. This solution was heated to reflux for 1 hour. The ethanol was then removed by rotary evaporation and the solution was acidified to pH 2 with hydrochloric acid. This aqueous solution was then extracted with 200 mL ethyl acetate, which was isolated, dried with magnesium sulfate, and concentrated to a white solid. This solid was then recrystallized from dichloromethane and hexane to yield 2 g (80% yield) of 2-propionic-3-methylmaleic anhydride.

B) Synthesis of 2,3-dioleoyldiaminopropionic ethylenediamine amide. 2,3-diaminopropionic acid (1.4 gm, 10 mmol) and dimethylaminopyridine (1.4 gm 11 mmol) were dissolved in 50 mL of water. To this mixture was added over 5 minutes with rapid stirring oleoyl chloride (7.7 mL, 22 mmol) of in 20 mL of tetrahydrofuran. After all of the acid chloride had been added, the solution was allowed to stir for 30 minutes. The pH of the solution was 4 at the end of the reaction. The tetrahydrofuran was removed by rotary evaporation. The mixture was then partitioned between water and ethyl acetate. The ethyl acetate was isolated, dried with magnesium sulfate, and concentrated by rotary evaporation to yield a yellow oil. The 2,3-dioleoyldiaminopropionic acid was isolated by silica gel chromatography, elution with ethyl ether to elute oleic acid, followed by 10% methanol 90% methylene chloride to elute diamide product, 1.2 g (19% yield). The diamide (1.1 gm, 1.7 mmol) was then dissolved in 25 mL of methylene chloride. To this solution was added N-hydroxysuccinimide (0.3 g. 1.5 eq) and dicyclohexylcarbodiimide (0.54 g, 1.5 eq). This mixture was allowed to stir overnight. The solution was then filtered through a cellulose plug. To this solution was added ethylene diamine (1 gm, 10 eq) and the reaction was allowed to proceed for 2 hours. The solution was then concentrated by rotary evaporation. The resulting solid was purified by silica gel chromatography elution with 10% ammonia saturated methanol and 90% methylene chloride to yield the triamide product 2,3-dioleoyldiaminopropionic ethylenediamine amide (0.1 gm, 9% yield). The triamide product was given the number MC213.

C) Synthesis of dioleylamideaspartic acid. N-(tert-butoxycarbonyl)-L-aspartic acid (0.5 gm, 2.1 mmol) was dissolved in 50 mL of acetonitrile. To this solution was added N-hydroxysuccinimide (0.54 gm, 2.2 eq) and was added dicyclohexylcarbodiimide (0.54 g, 1.5 eq). This mixture was allowed to stir overnight. The solution was then filtered through a cellulose plug. This solution was then added over 6 hours to a solution containing oleylamine (1.1 g, 2 eq) in 20 mL methylene chloride. After the addition was complete the solvents were removed by rotary evaporation. The resulting solid was partitioned between 100 mL ethyl acetate and 100 mL water. The ethyl acetate fraction was then isolated, dried by sodium sulfate, and concentrated to yield a white solid. The solid was dissolved in 10 mL of triflouroacetic acid, 0.25 mL water, and 0.25 mL triisopropylsilane. After two hours, the triflouroacetic acid was removed by rotary evaporation. The product was then isolated by silica gel chromatography using ethyl ether followed by 2% methanol 98% methylene chloride to yield 0.1 gm (10% yield) of pure dioleylamideaspartic acid, which was given the number MC303.

D) Synthesis of dimethylmaleamic-melittin and dimethylmaleamic-pardaxin. Solid melittin or pardaxin (100 μg) was dissolved in 100 μL of anhydrous dimethylformamide containing 1 mg of 2,3-dimethylmaleic anhydride and 6 μL of diisopropylethylamine.

E) Synthesis of polyethyleneglycol methyl ether 2-propionic-3-methylmaleate (CDM-PEG). To a solution of 2-propionic-3-methylmaleic anhydride (30 mg, 0.16 mmol) in 5 mL methylene chloride was added oxalyl chloride (200 mg, 10 eq) and dimethylformamide (1 μL). The reaction was allowed to proceed overnight at which time the excess oxalyl chloride and methylene chloride were removed by rotary evaporation to yield the acid chloride, a clear oil. The acid chloride was dissolved in 1 mL of methylene chloride. To this solution was added polyethyleneglycol monomethyl ether, molecular weight average of 5,000 (815 mg, 1 eq) and pyridine (20 μL, 1.5 eq) in 10 mL of methylene chloride. The solution was then stirred overnight. The solvent was then removed and the resulting solid was dissolved into 8.15 mL of water.

F) Synthesis of Polyvinyl(2-phenyl-4-hydroxymethyl-1, 3-dioxolane) from the reaction of Polyvinylphenyl Ketone and Glycerol. Polyvinyl phenyl ketone (500 mg, 3.78 mmol, Aldrich Chemical Company) was taken up in 20 mL dichloromethane. Glycerol (304 μL, 4.16 mmol, Acros Chemical Company) was added followed by p-toluenesulfonic acid monohydrate (108 mg, 0.57 mmol, Aldrich Chemical Company). Dioxane (10 mL) was added and the solution was stirred at room temperature overnight. After 16 hrs, TLC indicated the presence of ketone. The solution was concentrated under reduced pressure, and the residue dissolved in dimethylformamide (7 mL). The solution was heated to 60° C. for 16 hrs. After 16 hrs, TLC indicated the ketone had been consumed. Dialysis against $H_2O$ (1×3 L, 3500 MWCO), followed by lyophilization resulted in 606 mg (78%) of the ketal. Ketone was not observed in the sample by TLC analysis, however, upon treatment with acid, the ketone was again detected.

G) Peptide synthesis. Peptide syntheses were performed using standard solid phase peptide techniques using FMOC chemistry. N-terminal acryloyl 6-aminohexanoyl-KLLKLLLKLWLKLLKLLLKLL-$CO_2$ (AcKL$_3$; SEQ ID 8) was synthesized according to published procedure (O'Brien-Simpson, N. M., Ede, N. J., Brown, L. E., Swan, J., Jackson, D. C *J. Am. Chem. Soc.* 1997, 119, 1183).

H) Coupling KL$_3$ to poly(allylamine). To a solution of poly(allylamine) (2 mg) in water (0.2 mL) was added KL3 (0.2 mg, 2.5 eq) and 1-(3-dimethylaminopropyl)-3-ethylcarbodiimide hydrochloride (1 mg, 150 eq). The reaction was allowed to react for 16 h and then the mixture was placed into dialysis tubing and dialyzed against 3×1 L for 48 h. The solution was then concentrated by lyophilization to 0.2 mL.

I) Synthesis of aldehyde adduct of 2-propionic-3-methylmaleic anhydride (CDM-aldehyde). To a solution of 2-propionic-3-methylmaleic anhydride (CDM) 50 mg in 5 mL methylene chloride was added 1 mL oxalyl chloride. The solution was stirred overnight at room temperature. The excess oxalyl chloride and methylene chloride was removed by rotary evaporation to yield a clear oil. The oil was then dissolved in methylene chloride (5 mL) and 85 mg of 2,2-dimethoxyethylamine was added. The solution was added to proceed for 1 hour. The solvent was removed by rotary evaporation to yield a yellow oil which was placed under high vacuum (1 torr) for 24 hours. The resulting oil was dissolved in 5 mL water and chromatographed by reverse-phase HPLC eluting with acetonitrile containing 0.1% trifluoroacetic acid to produce the dimethyl acetal (20 mg).

To remove the acetal, it was dissolved in 1 mL acetonitrile and 0.1 mL concentrated hydrochloric acid. The aldehyde was isolated by reverse-phase HPLC eluting with acetonitrile containing 0.1% trifluoroacetic acid to produce 10 mg of aldehyde adduct of 2-propionic-3-methylmaleic anhydride (CDM-aldehyde).

J) Synthesis of mercaptoacetic acid thioester of 2-propionic-3-methylmaleic anhydride (CDM thioester). To a solution of 2-propionic-3-methylmaleic anhydride (CDM) 50 mg in 5 mL methylene chloride was added 1 mL oxalyl chloride. The solution was stirred overnight at room temperature. The excess oxalyl chloride and methylene chloride was removed by rotary evaporation to yield a clear oil. The oil was then dissolved in methylene chloride (5 mL) and 25 mg of mercaptoacetic acid was added, followed by the addition of 70 mg of diisopropylethylamine. After 1 hour, the solvent was removed by rotary evaporation and excess mercaptoacetic acid and diisopropylethylamine were removed by placing the sample under high vacuum (1 torr) for 24 hours. The resulting oil was dissolved in 5 mL water and chromatographed by reverse-phase HPLC eluting with acetonitrile containing 0.1% trifluoroacetic acid to produce the thioester.

Example 2

Synthesis of Polycations

A) Synthesis of L-cystine-1,4-bis(3-aminopropyl)piperazine copolymer. To a solution of N,N'-Bis(t-BOC)-L-cystine (85 mg, 0.15 mmol) in ethyl acetate (20 mL) was added N,N'-dicyclohexylcarbodiimide (108 mg, 0.5 mmol) and N-hydroxysuccinimide (60 mg, 0.5 mmol). After 2 hr, the solution was filtered through a cotton plug and 1,4-bis(3-aminopropyl)piperazine (54 μL, 0.25 mmol) was added. The reaction was allowed to stir at room temperature for 16 h. The ethyl acetate was then removed by rotary evaporation and the resulting solid was dissolved in trifluoroacetic acid (9.5 mL), water (0.5 mL) and triisopropylsilane (0.5 mL). After 2 h, the trifluoroacetic acid was removed by rotary evaporation and the aqueous solution was dialyzed in a 15,000 MW cutoff tubing against water (2×2 l) for 24 h. The solution was then removed from dialysis tubing, filtered through 5 μM nylon syringe filter and then dried by lyophilization to yield 30 mg of polymer.

B) Synthesis of adducts between peptide and poly-L-lysine adducts. To a solution of poly-L-lysine (10 mg, 0.2 μmol) and peptides KL$_3$ or melittin (2 μmol) is added 1-(3-dimethylaminopropyl)-3-ethylcarbodiimide hydrochloride (20 µmol). For the peptide KL₃, the reaction is performed in 2 mL of water. For the peptide melittin, the reaction is performed in a solution of 1 mL water and 1 mL triflouroethanol. The reaction is allowed to proceed overnight before placement into a 12,000 molecular weight cutoff dialysis bag and dialysis against 4×2 liters over 48 hours. The amount of coupled peptide is determined by the absorbance of the tryptophan residue at 280 nm, using an extinction coefficient of 5690 $cm^{-1}M^{-1}$ (Gill, S. C. and von Hippel, P. H. Analytical Biochemistry (1989) 182, 319–326). The conjugate of melittin and poly-L-lysine was determined to have 4 molecules of melittin per molecule of poly-L-lysine and is referred to as mel-PLL. The conjugate of $KL_3$ and poly-L-lysine was determined to have 10 molecules of $KL_3$ per molecule of poly-L-lysine and is referred to as $KL_3$-PLL.

C) Synthesis of adducts between peptide andpolyallylamine adducts. To a solution of polyallylamine (10 mg, 0.2 µmol) and peptides $KL_3$ or melittin (2 µmol) is added 1-(3-dimethylaminopropyl)-3-ethylcarbodiimide hydrochloride (20 µmol). For the peptide $KL_3$, the reaction is performed in 2 mL of water. For the peptide melittin, the reaction is performed in a solution of 1 mL water and 1 mL triflouroethanol. The reaction is allowed to proceed overnight before placement into a 12,000 molecular weight cutoff dialysis bag and dialysis against 4×2 liters over 48 hours to remove uncoupled peptide. The amount of coupled peptide is determined by the absorbance of the tryptophan residue at 280 nm, using an extinction coefficient of 5690 $cm^{-1}M^{-1}$ (Gill, S. C. and von Hippel, P. H. Analytical Biochemistry (1989) 182, 319–326). The conjugate melittin and polyallylamine was determined to have 4 molecules of melittin per molecule of polyallylamine and is referred to as mel-PAA. The conjugate of $KL_3$ and polyallylamine was determined to have 10 molecules of $KL_3$ per molecule of polyallylamine and is referred to as $KL_3$-PAA.

D) Synthesis of Di-(2-methyl-4-hydroxymethyl(glyoxilic acid ester)-1,3-dioxolane)-1,4-benzene: 1,4-Bis(3-aminopropyl)piperazine Copolymer (1:1) (MC228). To a solution of di-(2-methyl-4-hydroxymethyl(glyoxylic acid ester)-1,3-dioxolane) 1,4-benzene (100 mg, 0.273 mmol) in dimethylformamide was added 1,4-bis(3-aminopropyl)-piperazine (23 µL, 0.273 mmol, Aldrich Chemical Company) and the solution was heated to 80° C. After 16 hrs the solution was cooled to room temperature and precipitated with diethyl ether. The solution was decanted and the residue washed with diethyl ether (2×) and dried under vacuum to afford di-(2-methyl-4-hydroxymethyl(glyoxylic acid ester)-1,3-dioxolane) 1,4-benzene: 1,4-bis(3-aminopropyl)-piperazine copolymer (1:1).

By similar methods as example 2-D, the following polymers were constructed:

E) Di-(2-methyl-4-hydroxymethyl(succinic semialdehyde ester)-1,3-dioxolane)-1,4-benzene: 1,4-Bis(3-aminopropyl)piperazine Copolymer (1:1) (MC208).
F) Di-(2-methyl-4-hydroxymethyl(succinic semialdehyde ester)-1,3-dioxolane)-1,4-benzene: 1,4-Bis(3-aminopropyl)piperazine Copolymer (1:1) Reduced with $NaCNBH_3$ (MC301).
G) Di-(2-methyl-4-hydroxymethyl(succinic semialdehyde ester)-1,3-dioxolane)-1,4-benzene: 1,3-Diaminopropane Copolymer (1:1) (MC300).
H) Di-(2-methyl-4-hydroxymethyl(succinic semialdehyde ester)-1,3-dioxolane)-1,4-benzene: 3,3'-Diamino-N-methyldipropylamine Copolymer (1:1) (MC218).
I) Di-(2-methyl-4-hydroxymethyl(succinic semialdehyde ester)-1,3-dioxolane)-1,4-benzene: Tetraethylenepentamine Copolymer (1:1) (MC217).
J) Di-(2-methyl-4-hydroxymethyl(glyoxilic acid ester)-1,3-dioxolane)-1,4-benzene: 1,3-Diaminopropane Copolymer (1:1) (MC226).
K) Di-(2-methyl-4-hydroxymethyl(glyoxilic acid ester)-1,3-dioxolane)-1,4-benzene: 3,3'-Diamino-N-methyldipropylamine Copolymer (1:1) (MC227).
L) Synthesis of 1,4-Bis(3-aminopropyl)piperazine-Glutaric Dialdehyde Copolymer (MC140).

1,4-Bis(3-aminopropyl)piperazine (206 µL, 0.998 mmol, Aldrich Chemical Company) was taken up in 5.0 mL $H_2O$. Glutaric dialdehyde (206 µL, 0.998 mmol, Aldrich Chemical Company) was added and the solution was stirred at room temperature. After 30 min, an additional portion of $H_2O$ was added (20 mL), and the mixture neutralized with 6 N HCl to pH 7, resulting in a red solution. Dialysis against $H_2O$ (3×3 L, 12,000–14,000 MWCO) and lyophilization afforded 38 mg (14%) of the copolymer.

By similar methods as example 2 L, the following polymers were constructed:

M) Diacetylbenzene-1,3-Diaminopropane Copolymer (1:1) (MC321)
N) Diacetylbenzene-Diamino-N-methyldipropylamine Copolymer (1:1) (MC322).
O) Diacetylbenzene-1,4-Bis(3-aminopropyl)piperazine Copolymer (1:1) (MC229)
P) Diacetylbenzene-Tetraethylenepentamine Copolymer (1:1) (MC323).
Q) Glutaric Dialdehyde-1,3-Diaminopropane Copolymer (1:1) (MC324)
R) Glutaric Dialdehyde-Diamino-N-methyldipropylamine Copolymer (1:1) (MC325).
S) Glutaric Dialdehyde-Tetraethylenepentamine Copolymer (1:1) (MC326).
T) 1,4-Cyclohexanone-1,3-Diaminopropane Copolymer (1:1) (MC330)
U) 1,4-Cyclohexanone-Diamino-N-methyldipropylamine Copolymer (1:1) (MC331).
V) 1,4-Cyclohexanone-1,4-Bis(3-aminopropyl)piperazine Copolymer (1:1) (MC312)
W) 1,4-Cyclohexanone-Tetraethylenepentamine Copolymer (1:1) (MC332).
X) 2,4-Pentanone-1,4-Bis(3-aminopropyl)piperazine Copolymer (1:1) (MC340)
Y) 2,4-Pentanone-Tetraethylenepentamine Copolymer (1:1) (MC347).
Z) 1,5-Hexafluoro-2,4-Pentanone-1,4-Bis(3-aminopropyl)piperazine Copolymer (1:1) (MC339)
AA) 1,5-Hexafluoro-2,4-Pentanone-Tetraethylenepentamine Copolymer (1:1) (MC346).
BB) Synthesis of Di-(2-methyl-4-aminomethyl-1,3-dioxolane)-1,4-benzene-Glutaric Dialdehyde Copolymer (MC352). To a solution of di-(2-methyl-4-aminomethyl-1,3-dioxolane)-1,4-benzene (23 mg, 75 µmol) in dimethylformamide (200 µL) was added glutaric dialdehyde (7.5 mg, 75 µmol, Aldrich Chemical Company). The reaction mixture was heated at 80° C. for 6 hrs under nitrogen. The solution was cooled to room temperature and used without further purification.

CC) Synthesis of Di-(2-methy-4-hydroxymethyl(glycine ester)-1,3-dioxolane)-1,4,benzene-Glutaric Dialdehyde Copolymer (MC357). To a solution of di-(2-methy-4-hydroxymethyl(glycine ester)-1,3-dioxolane)-1,4,benzene (35 mg, 82 µmol) in dimethylformamide (250 µL) was added glutaric dialdehyde (8.2 mg, 82 µmol, Aldrich Chemical Company). The reaction mixture was heated at 80° C. for 12 hrs. The solution was cooled to room temperature and used without further purification.

DD) Synthesis of a Silyl Ether from Polyvinylalcohol and 3-Aminopropyltrimethoxysilane (MC221). To a solution of polyvinylalcohol (520 mg, 11.8 mmol (OH), 30,000–70,000 MW, Sigma Chemical Company) in dimethylformamide (4 mL) was added 3-aminopropyltrimethoxysilane (1.03 mL, 5.9 mmol, Aldrich Chemical Company) and the solution was stirred at room temperature. After 2.5 hrs, a 20 μL aliquot of the reaction mixture was removed and added to pDNA (pCI Luc) (100 μg) in 25 mM HEPES buffer at pH 7.5 (500 μL) to test for polyamine formation (pDNA:amine 1:3). Particle sizing (Brookhaven Instruments Coporation, ZetaPlus Particle Sizer, 190, 532 nm) indicated an effective diameter of 3000 nm (1.3 mcps) indicating pDNA condensation and particle formation. An aliquot of 1 N HCl (40 μL) was added to the sample, and the particle size was again measured. After 1 min of exposure to the acidic conditions, the particle size was 67,000 nm (600 kcps). After 10 min, particles were no longer present within the sample. The sample was dried under high vacuum to afford 1.0 g (83%) white solid.

By similar methods as example 2-DD, the following polymers were constructed:

EE) Silyl Ether from Poly-L-Arginine/-L-Serine(3:1) and 3-Aminopropyltrimethoxysilane (2:1) (MC358).
  Poly-L-Arginine/-L-Serine(3:1) (20,000–50,000 MW, Sigma Chemical Company)
  3-Aminopropyltrimethoxysilane (Aldrich Chemical Company)

FF) Silyl Ether from Poly-DL-Serine and 3-Aminopropyltrimethoxysilane (3:1) (MC366).
  Poly-DL-Serine (5,000–15,000 MW, Sigma Chemical Company)
  3-Aminopropyltrimethoxysilane (Aldrich Chemical Company)

GG) Silyl Ether from Poly-DL-Serine and 3-Aminopropyltrimethoxysilane (2:1) (MC367).
  Poly-DL-Serine (5,000–15,000 MW, Sigma Chemical Company)
  3-Aminopropyltrimethoxysilane (Aldrich Chemical Company)

HH) Silyl Ether from Poly-DL-Serine and N-[3-(Triethoxysilyl)propyl]-4,5-dihydroimidizole (3:1) (MC369).
  Poly-DL-Serine (5,000–15,000 MW, Sigma Chemical Company)
  N-[3-(Triethoxysilyl)propyl]-4,5-dihydroimidizole (United Chemical Technologies, Inc.)

II) Silyl Ether from Poly-DL-Serine and N-Trimethoxysilylpropyl-N,N,N-trimethylammonium chloride (3:1) (MC370).
  Poly-DL-Serine (5,000–15,000 MW, Sigma Chemical Company)
  N-Trimethoxysilylpropyl-N,N,N-trimethylammonium chloride (United Chemical Technologies, Incorporated)

JJ) Silazane from Poly-L-Lysine and 3-Aminopropyltrimethoxysilane (2:1) (MC360).

KK) Poly(1,1-Dimethylsilazane) Tolemer (MC222).
  Sample was obtained from United Chemical Technologies, Incorporated.

LL) Synthesis of 5,5'-Dithiobis(2-nitrobenzoic acid)-1,4-Bis(3-aminopropyl)piperazine Copolymer. 1,4-Bis(3-aminopropyl)piperazine (10 mL, 0.050 mmol, Aldrich Chemical Company) was taken up in 1.0 mL methanol and HCl (2 mL, 1 M in Et2O, Aldrich Chemical Company) was added. Et2O was added and the resulting HCl salt was collected by filtration. The salt was taken up in 1 mL DMF and 5,5'-dithiobis[succinimidyl(2-nitrobenzoate)] (30 mg, 0.050 mmol) was added. The resulting solution was heated to 80° C. and diisopropylethylamine (35 mL, 0.20 mmol, Aldrich Chemical Company) was added by drops. After 16 hr, the solution was cooled, diluted with 3 mL H2O, and dialyzed in 12,000–14,000 MW cutoff tubing against water (2×2 L) for 24 h. The solution was then removed from dialysis tubing and dried by lyophilization to yield 23 mg (82%) of 5,5'-dithiobis(2-nitrobenzoic acid)-1,4-bis(3-aminopropyl)piperazine copolymer.

MM) Synthesis of cysteine-modified polycations. The N-hydroxysuccinimide (HHS) ester of Nα-Fmoc-S-tert-butylthio-L-cysteine was generated by reaction of protected amino acid with dicyclohexylcarbodiimide (DCC) and NHS in acetonitrile. After 16 hours, the dicyclohexylurea is filtered off. The polycation is dissolved in methanol, ca 10 mg/ml, by the addition of 1 equivalent of diisopropylethylamine. To this polycation solution is added the NHS ester in acetonitrile. After 1 hour, the modified polycation is precipitated out by the addition of ethyl ether. The modified polycation is then dissolved in piperidine and methanol (50/50). After 30 minutes, the cysteine-modified polycation is precipitated out by the addition of ethyl ether and then dissolved to 10 mg/ml in water. The pH of the solution is then reduced by the addition of concentrated hydrochloric acid to reduce the pH to 2.

NN) Synthesis of Amine-Containing Enol Ether Copolymers or Poly(Alkyl enolether-co-vinyloxy Ethylamine) Polymers Synthesis of 2-(-vinyloxy)ethyl phthalimide(ImVE): ImVE was prepared by reacting 2-chloroethyl vinyl ether(25 g, 0.24 mol) with potassium phthalimide(25 g, 0.135 mol) in dimethyl foramide(75 mL) using tetra-n-butyl ammonium bromide as a phase transfer catalyst. This reaction mixture was stirred at 100° C. for 6 hours then poured into 800 mL of distilled water, and filtered and washed with a large amount of distilled water. The recovered yellowish crystal where then recrystallized twice from methanol to give white crystal's, which were then dried for 48 hrs under reduced pressure.

Polymerization Procedures: The polymerization were carried out in anhydrous methylene chloride at −78° C. under a blanket of dry nitrogen gas in oven-dried glassware. The reaction is initiated by adding borontrifluoride diethyl etherate to ImVE, and a mixture of enol ethers. The reaction is allowed to run for 3 hours at −78° C., and then allowed to warm for ten minutes at room temperature, and then quenched with prechilled ammonia saturated methanol. The product was then evaporated to dryness under reduced pressure to give the product polymers.

Hydrazinolysis of Polymers: The polymer is then dissolved in a 1,4-dioxane(2)/methanol mixture and 10 equivalents (eq.) of hydrazine hydrate per mole of amine present. This solution is then refluxed for 2 hours, and cooled to room temperature, and the solvent is then removed under reduced pressure. This solution is then brought up in 0.5M HCl, and refluxed for 60 minutes. The cooled solution is then transferred to 3,000 $M_w$ dialysis tubing and dialyzed(4×5 L) for 48 hours. This solution is then frozen and lyophilized down to solid.

Table of polymers synthesized

| Polymer # | BF₃EtOEt | ImVE eq. added | Octadecyl enol ether eq. added | Ethyl enol ether eq. added | Butyl enol Ether eq. added |
|---|---|---|---|---|---|
| DW#291 | 2% | 0.875 | 0.03 | 0.095 | — |
| DW#301 | 2% | 0.75 | 0.03 | — | 0.22 |
| DW#290 | 2% | 0.97 | 0.03 | — | — |
| DW#297* | 2% | 0.97 | 0.03 | — | — |

*DW#297 is DW#290 that has been modified with 0.3 Eq of Lactobionic Acid via EDC/NHS coupling. See following procedure.

Poly(alkyl enolether-co-vinyloxy ethylamine) graft lactobionic acid polycation (DW#297) DW#290 (15,000 MW) is dissolved to 50 mg/mL in 100 mM MES (pH 6.5) buffer in a 15-ml polypropylene tube. To this solution is added 0.3 molar equivalent (relative to amine content of DW#290) of lactobionic acid acid. N-(3-Dimethylaminopropyl)-N'-ethyl-carbodiimide (EDC) (0.33 equivalent) and N-hydroxysuccinimide (0.33 equivalent) are dissolved in 2 ml of MES buffer and are added immediately to the solution containing DW#290. The reaction tube was sealed and allowed to react at room temperature for 24 hours. The reaction mixture is then removed from tube and placed into dialysis tubing (3,500 MW cutoff), and dialyzed against 7×4 L water over a one week period. The polymer is then removed from the tubing and concentrated by lyophilization to 10 mg/mL. This polymer is given the number DW#297.

Example 3

Synthesis of Polyanions

A) Synthesis of 2,3-dimethylmaleamic poly-L-lysine. Poly-L-lysine (10 mg 34,000 MW Sigma Chemical) was dissolved in 1 mL of aqueous potassium carbonate (100 mM). To this solution was added 2,3-dimethylmaleic anhydride (100 mg, 1 mmol) and the solution was allowed to react for 2 hr. The solution was then dissolved in 5 mL of aqueous potassium carbonate (100 mM) and dialyzed against 3×2 L water that was at pH8 with addition of potassium carbonate. The solution was then concentrated by lyophilization to 10 mg/mL of 2,3-dimethylmaleamic poly-L-lysine.

B) General procedure for the reaction of mel-PAA, KL₃-PAA, mel-PLL, and KL₃-PLL with dimethylmaleic anhydride and 2-propionic-3-methylmaleic anhydride. Peptide-polycation conjugates (10 mg/mL) in water were reacted with a ten-fold weight excess of dimethylmaleic anhydride and a ten-fold weight excess of potassium carbonate. Analysis of the amine content after 30 by addition of peptide solution to 0.4 mM trinitrobenzene sulfonate and 100 mM borax revealed no detectable amounts of amine.

C) Synthesis of Polyvinyl(2-methyl-4-hydroxymethyl (succinic anhydride ester)-1,3-dioxolane. To a solution of polyvinyl(2-methyl-4-hydroxymethyl-1,3-dioxolane) (220 mg, 1.07 mmol) in dichloromethane (5 mL) was added succinic anhydride (161 mg, 1.6 mmol, Sigma Chemical Company), followed by diisopropylethyl amine (0.37 mL, 2.1 mmol, Aldrich Chemical Company) and the solution was heated at reflux. After 16 hrs, the solution was concentrated, dialyzed against H₂O (1×3 L, 3500 MWCO), and lyophilized to afford 250 mg (75%) of the ketal acid polyvinyl (2-methyl-4-hydroxymethyl(succinic anhydride ester)-1,3-dioxolane.

D) Synthesis of Ketal from Polyvinyl Alcohol and 4-Acetylbutyric Acid. Polyvinylalcohol (200 mg, 4.54 mmol, 30,000–60,000 MW, Aldrich Chemical Company) was taken up in dioxane (10 mL). 4-acetylbutyric acid (271 µL, 2.27 mmol, Aldrich Chemical Company) was added followed by p-toluenesulfonic acid monohydrate (86 mg, 0.45 mmol, Aldrich Chemical Company). After 16 hrs, TLC indicated the presence of ketone. The solution was concentrated under reduced pressure, and the residue dissolved in dimethylformamide (7 mL). The solution was heated to 60° C. for 16 hrs. After 16 hrs, TLC indicated the loss of ketone in the reaction mixture. Dialysis against H₂O (1×4 L, 3500 MWCO), followed by lyophilization resulted in 145 mg (32%) of the ketal. Ketone was not observed in the sample by TLC analysis, however, upon treatment with acid, the ketone was again detected.

E) Partial Esterification of Poly-Glutamic Acid with Di-(2-methyl-4-hydroxymethyl-1,3-dioxolane)-1,4-benzene (MC 196). To a solution of poly-L-glutamic acid (103 mg, 792 µmol, 32,000 MW, Sigma Chemical Company) in sodium phosphate buffer (30 mM) was added 1-(3-dimethylaminopropyl)-3-ethylcarbodiimide hydrochloride (129 mg, 673 µmol, Aldrich Chemical Company), followed by di-(2-methyl-4-hydroxymethyl-1,3-dioxolane)-1,4-benzene (25.0 mg, 80.5 µmol), and a catalytic amount of 4-dimethylaminopyridine. After 12 hrs, the reaction mixture was dialyzed against water (2×1 L, 12,000–14,000 MWCO) and lyophilized to afford 32 mg of poly-glutamic acid partially esterified with di-(2-methyl-4-hydroxymethyl-1,3-dioxolane)-1,4-benzene.

F) Aldehyde Derivatization of the Poly-Glutamic Acid Partially Esterified with Di-(2-methyl-4-hydroxymethyl-1,3-dioxolane)-1,4-benzene. To a solution of succinic semialdehyde (2.4 mg, 23 µmol, Aldrich Chemical Company) in water (100 µL) was added 1-(3-dimethylaminopropyl)-3-ethylcarbodiimide hydrochloride (4.7 mg, 2.4 µmol, Aldrich Chemical Company) followed by N-hydroxysuccinimide (2.8 mg, 24 µmol, Aldrich Chemical Company). The reaction was stirred at room temperature for 20 min. Formation of the N-hydroxysuccinic ester of succinic semialdehyde was confirmed by mass spectrometry.

Poly-glutamic acid partially esterified with di-(2-methyl-4-hydroxymethyl-1,3-dioxolane)-1,4-benzene (15.0 mg, 115 µmol) was taken up in water (100 µL) and added to the N-hydroxysuccinic ester of succinic semialdehyde, followed by a crystal of 4-dimethyl-aminopyridine. The reaction mixture was stirred overnight at room temperature. After 12 hrs the reaction mixture was dialyzed against water (2×1 L, 12,000–14,000 MWCO) and lyophilized to afford 3.0 mg. After dialysis the product tested positive for aldehyde content with 2,4-di-nitrophenylhydrazine.

G) Synthesis of polypropylacrylic acid. To a solution of diethylpropylmalonate (2 g, 10 mmol) in 50 mL ethanol was added potassium hydroxide (0.55 g, 1 eq) and the mixture was stirred at room temperature for 16 hours. The ethanol was then removed by rotary evaporation. The reaction mixture was partitioned between 50 mL ethyl acetate and 50 mL of water. The aqueous solution was isolated, and acidified with hydrochloric acid. The solution was again partitioned between ethyl acetate and water. The ethyl acetate layer was isolated, dried with sodium sulfate, and concentrated to yield a clear oil. To this oil was added 20 mL of pyridine, paraformaldehyde (0.3 g, 10 mmol), and 1 mL piperidine. The mixture was refluxed at 130° C. until the evolution of gas was observed, ca. 2 hours. The ester product was then dissolved into 100 mL ethyl ether, which was washed with 100 mL 1 M hydrochloric acid, 100 mL water, and 100 mL saturated sodium bicarbonate. The ether layer was isolated, dried with magnesium sulfate, and concentrated by rotary evaporation to yield a yellow oil. The ester was then hydrolyzed by dissolving in 50 mL ethanol with addition of potassium hydroxide (0.55 gm, 10 mmol). After 16 hours, the reaction mixture was acidified by the addition of hydrochloric acid. The propylacrylic acid was purified by vacuum distillation (0.9 g, 80% yield), boiling point of product is 60° C. at 1 torr.

The propylacrylic acid was polymerized by addition of 1 mole percent of azobisisobutyonitrile and heating to 60° C. for 16 hours. The polypropylacrylic acid was isolated by precipitation with ethyl ether.

H) Synthesis of 5,5'-Dithiobis(2-nitrobenzoic acid)-Poly-Glutamicacid (8mer) Copolymer. H$_2$N-EEEEEEEE-NHCH$_2$CH$_2$NH$_2$ (SEQ ID 10; 5.0 mg, 0.0052 mmol, Genosis) was taken up in 0.1 mL HEPES (250 mM, pH 7.5). 5,5'-dithiobis[succinimidyl(2-nitrobenzoate)] (3.1 mg, 0.0052) was added with 0.2 mL DMSO and the mixture was stirred overnight at room temperature. After 16 hr the solution was heated to 70° C. for 10 min, cooled to room temperature and diluted to 1.10 mL with DMSO.

Example 4

Synthesis of Acid Labile Monomers

A) Synthesis of Di-(2-methyl-4-hydroxymethyl-1,3-dioxolane)-4-benzene (MC 216). To a solution of diacetylbenzene (2.00 g, 12.3 mmol, Aldrich Chemical Company) in toluene (30.0 mL), was added glycerol (5.50 g, 59.7 mmol, Acros Chemical Company) followed by p-toluenesulfonic acid monohydrate (782 mg, 4.11 mmol, Aldrich Chemical Company). The reaction mixture was heated at reflux for 5 hrs with the removal of water by azeotropic distillation in a Dean-Stark trap. The reaction mixture was concentrated under reduced pressure, and the residue was taken up in Ethyl Acetate. The solution was washed 1×10% NaHCO$_3$, 3×H$_2$O, 1× brine, and dried (MgSO$_4$). Following removal of solvent (aspirator), the residue was purified by flash chromatography on silica gel (20×150 mm, CH$_2$Cl$_2$ eluent) to afford 593 mg (16% yield) of di-(2-methyl-4-hydroxymethyl-1,3-dioxolane)-1,4-benzene. Molecular ion calculated for C$_{16}$H$_{22}$O$_6$ 310, found m+1/z 311.2; 300 MHz NMR (CDCl$_3$, ppm) δ 7.55–7.35(4H, m) 4.45–3.55 (10H, m) 1.65 (6H, brs).

B) Synthesis of Di-(2-methyl-4-hydroxymethyl(succinic semialdehyde ester)-1,3-dioxolane)-1,4-benzene (MC 211). To a solution of succinic semialdehyde (150 mg, 1.46 mmol, Aldrich Chemical Company) and di-(2-methyl-4-hydroxymethyl-1,3-dioxolane)-1,4-benzene (150 mg, 480 μmol) in CH$_2$Cl$_2$ (4 mL) was added dicyclohexylcarbodiimide (340 mg, 1.65 mmol, Aldrich Chemical Company) followed by a catalytic amount of 4-dimethylaminopyridine. The solution was stirred for 30 min and filtered. Following removal of solvent (aspirator), the residue was purified by flash chromatography on silica gel (20×150 mm, CH$_2$Cl$_2$ eluent) to afford 50 mg (22%) of di-(2-methyl-4-hydroxymethyl(succinic semialdehyde ester)-1,3-dioxolane)-1,4-benzene. Molecular ion calculated for C$_{24}$H$_{30}$O$_{10}$ 478.0 found m+1/z 479.4.

C) Synthesis of Di-(2-methyl-4-hydroxymethyl(glyoxilic acid ester)-1,3-dioxolane)-1,4-benzene (MC225). To a solution of glyoxylic acid monohydrate (371 mg, 403 μmol, Aldrich Chemical Company) and di-(2-methyl-4-hydroxymethyl-1,3-dioxolane)-1,4-benzene (500 mg, 161 μmol) in dimethylformamide (8 mL) was added dicyclohexylcarbodiimide (863 mg, 419 μmol, Aldrich Chemical Company). The solution was stirred for 30 min and filtered. Following removal of solvent (aspirator), the residue was purified by flash chromatography on silica gel (20×150 mm, ethylacetate/Hexanes (1:2.3 eluent) to afford 58 mg (10%) of di-(2-methyl-4-hydroxymethyl(glyoxylic acid ester)-1,3-dioxolane)-1,4-benzene.

D) Synthesis of Di-(2-methyl-4-aminomethyl-1,3-dioxolane)-1,4-benzene (MC372). To a solution of 1,4-diacetylbenzene (235 mg, 1.45 mmol, Aldrich Chemical Company) in toluene (15.0 mL) was added 3-amino-1,2-propanediol protected as the FMOC carbamide (1.0 g, 3.2 mmol), followed by a catalytic amount of p-toluenesulfonic acid monohydrate (Aldrich Chemical Company). The reaction mixture was heated at reflux for 16 hrs with the removal of water by azeotropic distillation in a Dean-Stark trap. The reaction mixture was cooled to room temperature, partitioned in toluene/H$_2$O, washed 1×10% NaHCO$_3$, 3×H$_2$O, 1×brine, and dried (MgSO$_4$). The extract was concentrated under reduced pressure and crystallized (methanol/H$_2$O). The protected amine ketal was identified in the supernatant, which was concentrated to afford 156 mg product. The free amine was generated by treating the ketal with piperidine in dichloromethane for 1 hr.

E) Synthesis of Di-(2-methyl-4-hydroxymethyl(glycine ester)-1,3-dioxolane)-1,4-benzene (MC373). To a solution of FMOC-Glycine (690 mg, 2.3 mmol, NovaBiochem) in dichloromethane (4.0 mL) was added dicyclohexylcarbodiimide (540 mg, 2.6 mmol, Aldrich Chemical Company). After 5 minutes, di-(2-methyl-4-hydroxymethyl-1,3-dioxolane)-1,4-benzene (240 mg, 770 μmol) was added followed by a catalytic amount of 4-dimethylaminopyridine. After 20 min, the reaction mixture was filtered and concentrated (aspirator) to afford 670 mg of oil. The residue was taken in tetrahydrofuran (4.0 mL) and piperidine (144 mg, 1.7 mmol) was added. The reaction was stirred at room temperature for 1 hr and added to cold diethyl ether. The resulting solid was washed 3× diethyl ether to afford di-(2-methy-4-hydroxymethyl(glycine ester)-1,3-dioxolane)-1,4,benzene. Molecular ion calculated for C$_{20}$H$_{28}$N$_2$O$_8$ 424, found m+1/z 425.2.

Example 5

Synthesis of Polyampholytes

A) Synthesis of Poly-L-Glutamic acid (octamer)-Glutaric Dialdehyde Copolymer (MC151).

H$_2$N-EEEEEEEE-NHCH$_2$CH$_2$NH$_2$ (SEQ ID 10; 5.5 mg, 0.0057 mmol, Genosis) was taken up in 0.4 mL H$_2$O. Glutaric dialdehyde (0.52 μL, 0.0057 mmol, Aldrich Chemical Company) was added and the mixture was stirred at room temperature. After 10 min the solution was heated to 70° C. After 15 hrs, the solution was cooled to room temperature and dialyzed against H$_2$O (2×2 L, 3500 MWCO). Lyophilization afforded 4.3 mg (73%) polyglutamic acid (octamer)-glutaric dialdehyde copolymer.

B) Synthesis of poly N-terminal acryloyl 6-aminohexanoyl-KLLKLLLKLWLKLLKLLLKLL-CO$_2$ (pAcKL$_3$; SEQ ID 8). A solution of AcKL3 (20 mg, 7.7 μmol) in 0.5 mL of 6M guanidinium hydrochloride, 2 mM EDTA, and 0.5 M Tris pH 8.3 was degassed by placing under a 2 torr vacuum for 5 minutes. Polymerization of the acrylamide was initiated by the addition of ammonium persulfate (35 μg, 0.02 eq.) and N,N,N,N-tetramethylethylenediamine (1 μL). The polymerization was allowed to proceed overnight. The solution was then placed into dialysis tubing (12,000 molecular weight cutoff) and dialyzed against 3×2 L over 48 hours. The amount of polymerized peptide (6 mg, 30% yield) was determined by measuring the absorbance of the tryptophan residue at 280 nm, using an extinction coefficient of 5690 cm$^{-1}$M$^{-1}$ (Gill, S. C. and von Hippel, P. H. Analytical Biochemistry (1989) 182, 319–326).

C) Formation of pH-labile polyampholytes using CDM thioester and cysteine-modified polycations. A pH-labile polyanion is generated by the reaction of a polyamine with 2 equivalents (relative amines) of CDM thioester. The cysteine-modified polycation is deprotected by reduction of disulfide with dithiothreitol. The thioester-containing, pH-labile polyanion is added to the cysteine-modified polycation. The thioester groups and cysteine groups react to produce a pH-labile polyampholyte. In addition, DNA may be condensed by the cysteine-modified polycation prior to the addition of the thioester-containing, pH-labile polyanion to produce a DNA-polyampholyte complex. Polycations that have been modified with cysteine and used as pH-labile polyanion are PLL, polyallylamine, polyvinylamine, polyethyleneimine, and histone H1. DNA-containing complexes formed using this procedure have been found to be 100 nm in size, which is stable upon the addition of 150 mM NaCl.

Example 6

In Vitro Transfections with pH-Labile Polyampholytes

A) In Vitro Transfection with DNA-PLL complexes with dimethylmaleamic KL$_3$ and dimethylmaleamic KL$_3$-PLL. To a complex of plasmid DNA pCIluc (10 µg/mL, prepared according to Danko, I., Williams, P., Herweijer, H. Zhang, G., Latendresse, J. S., Bock, I., Wolff, J. A. *Hum. Mol. Genetics* 1997, 6, 1435.) and poly-L-lysine (40 µg/mL) in 0.5 mL water was added 10 mg of 2,3-dimethylmaleamic -KL$_3$-PLL or 2,3-dimethylmaleamic -KL$_3$. The DNA-poly-L-lysine-2,3-dimethylmaleamic peptide complexes were then added (200 µL) to a well containing 3T3 mouse embryonic fibroblast cells in opti-MEM. After 4 h, the media was replaced with 90% Dubelco's modified Eagle Media and 10% fetal bovine serum the cells were then allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| 2,3-dimethylmaleamic peptide | Relative Light Units |
|---|---|
| 2,3-dimethylmaleamic KL$_3$ | 20927 |
| 2,3-dimethylmaleamic KL$_3$-PLL | 130478 |

B) In Vitro Transfection with DNA-PLL complexes with dimethylmaleamic KL$_3$-PLL, 2-propionic-3-methylmaleamic KL$_3$-PLL, and succinimic KL$_3$-PLL. To a complex of plasmid DNA pCIluc (10 µg/mL, prepared according to Danko, I., Williams, P., Herweijer, H. Zhang, G., Latendresse, J. S., Bock, I., Wolff, J. A. *Hum. Mol. Genetics* 1997, 6, 1435.) and poly-L-lysine (40 µg/mL) in 0.5 mL water was added 25 µg of 2,3-dimethylmaleamic -KL$_3$-PLL, 2-propionic-3-methylmaleamic KL$_3$-PLL, and succinimic KL$_3$-PLL. The DNA-poly-L-lysine-peptide complexes were then added (200 µL) to a well containing 3T3 mouse embryonic fibroblast cells in opti-MEM media. After 4 h, the media was replaced with 90% Dubelco's modified Eagle Media and 10% fetal bovine serum the cells were then allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Modified peptide | Relative Light Units |
|---|---|
| 2,3-dimethylmaleamic KL$_3$-PLL | 96221 |
| 2-propionic-3-methylmaleamic KL$_3$-PLL | 102002 |
| succinimic KL$_3$-PLL | 21206 |

C) Transfection of 3T3 Cells with Dioleoyl 1,2-Diacyl-3-Trimethylammonium-Propane (DOTAP) and the membrane active peptide KL3 conjugated to dimethylmaleic modified Polyallylamine (DM-PAA-KL3) and poly-L-lysine or L-cystine-1,4-bis(3-aminopropyl)piperazine copolymer.

Three complexes were formed:

Complex I) To 250 µL 25 mM HEPES pH8.0 was added DOTAP 300 µg, Avanti Polar Lipids)

Complex II) To 250 µL 25 mM HEPES pH8.0 was added DOTAP (300 µg, Avanti Polar Lipids) followed by DM-PAA-KL$_3$ (10 µg) followed by poly-L-lysine (10 µg, Sigma).

Complex III) To 250 µL 25 mM HEPES pH8.0 was added DOTAP (300 µg, Avanti Polar Lipids) followed by DM-PAA-KL$_3$ (10 µg) followed by L-cystine-1,4-bis(3-aminopropyl)piperazine copolymer (10 µg).

Liposomes for each complex were formed by 5 minutes of bath sonication then purified in batch by addition of 250 µl of DEAE sephadex A-25. DNA (25 ug, pCILuc) was then added to the supernatant containing the purified liposomes of each complex.

Transfections were carried out in 35 mm wells. At the time of transfection, 3T3 cells, at approximately 60% confluency, stored in complete growth media, DMEM with 10% fetal bovine serum (Sigma). 50 µL of complex was added to each well. After an incubation of 48 hours, the cells were harvested and the lysate was assayed for luciferase expression as previously reported (Wolff, J. A., Malone, R. W., Williams, P., Chong, W., Acsadi, G., Jani, A. and Felgner, P. L.

Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Results: | |
|---|---|
| Complex I: RLU = | 167 |
| Complex II: RLU = | 60,092 |
| Complex III: RLU = | 243,986 |

The 2,3-dimethylmaleic modification of DM-PAA-KL3 allows the polymer to complex with the cationic polymer L-cystine-1,4-bis(3-aminopropyl)piperazine copolymer and then cleavage of the 2,3-dimethylmaleamic group to release and reactivate in the disulfide reducing environment encountered by the complex in the cell. This caused a significant increase in luciferase expression over either DOTAP complexes alone or DM-PAA-KL3 complexed with poly-L-lysine that will not cleave in the reducing environment encountered by the complex in the cell.

D) In Vitro Transfection with DNA-PLL-KL$_3$ and dimethylmaleamic KL$_3$. To a complex of plasmid DNA pCIluc (10 μg/mL, 0.075 mM in phosphate, 2.6 μg/μL pCIluc; prepared according to Danko, I., Williams, P., Herweijer, H. Zhang, G., Latendresse, J. S., Bock, I., Wolff, J. A. *Hum. Mol. Genetics* 1997, 6, 1435.) and poly-L-lysine (40 μg/mL) in 0.5 mL of 5 mM HEPES pH 7.5 was added succinylated poly-L-lysine (34,000 MW, Aldrich Chemical), 2,3-dimethylmaleamic melittin and 2,3-dimethylmaleamic KL$_3$. The DNA-poly-L-lysine-2,3-dimethylmaleamic peptide complexes were then added (200 μL) to wells containing 3T3 mouse embryonic fibroblast cells in 290 mM glucose and 5 mM HEPES buffer pH 7.5. After 1.5 h, the glucose media was replaced with Dubelco's modified Eagle Media and the cells were allowed to incubate for 48 h. The cells were then harvested and then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Peptide | Relative Light Units (Relative to Succinylated poly-L-lysine) |
|---|---|
| Succinylated poly-L-lysine | 6410 (1) |
| KL$_3$ | 261 (0.04) |
| 2,3-dimethylmaleamic KL$_3$ | 49535 (7.7) |

E) Transfection of HELA Cells with Histone H1 and the Membrane Active Peptide Melittin, Dimethylmaleic Modified Melittin or Succinic Anhydride Modifed Melittin.

Three complexes were formed:

Complex I) To 300 μL Opti-MEM was added Histone H1(12 μg, Sigma Corporation) followed by the peptide Melittin (20 μg) followed by pDNA (pCI Luc, 4 μg).

Complex II) To 300 μL Opti-MEM was added Histone H1(12 μg, Sigma Corporation) followed by the 2,3-dimethylmaleic modified peptide Melittin (20 μg) followed by pDNA (pCI Luc, 4 μg).

Complex III) To 300 μL Opti-MEM was added Histone H1(12 μg, Sigma Corporation) followed by the succinic anhydride modified peptide Melittin (20 μg) followed by pDNA (pCI Luc, 4 μg).

Transfections were carried out in 35 mm wells. At the time of transfection, HELA cells, at approximately 60% confluency, stored in complete growth media, DMEM with 10% fetal bovine serum (Sigma). 150 μL of complex was added to each After an incubation of 48 hours, the cells were harvested and the lysate was assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for two separate wells of cells.

| Results: | |
|---|---|
| Complex I: RLU = | 2,161 |
| Complex II: RLU = | 105,909 |
| Complex III: RLU = | 1,056 |

The 2,3-dimethylmaleic modification of the peptide melittin caused a significant increase in luciferase expression over either unmodified melittin peptide or melittin peptide modified with succinic anhydride which will not be cleave in lowered pH.

F) In vitro Transfection using pH-labile polyampholytes. Polycations DW291, DW301, and DW323 were partially modified by reaction with CDM or dimethylmaleic anhydride (DM) according to the following table. To ensure the pH was not acidic, a 25-fold weight excess of HEPES base was added to samples (relative to anhydride). In all cases, the amount of anhydride was less than the amount of amines, which means that the modified polymers were polyampholytes, containing both amines and carboxylate groups.

To a solution of plasmid DNA pCIluc (10 μg/mL, prepared according to Danko, I., Williams, P., Herweijer, H. Zhang, G., Latendresse, J. S., Bock, I., Wolff, J. A. *Hum. Mol. Genetics* 1997, 6, 1435.) in 0.25 mL of 5 mM HEPES buffer pH 7.5 was added 40 μg/mL polyampholytes. These complexes were then added (100 μL) to a well (12-well plates containing 1 mL media) containing mouse hepatoma hepa-1clc7 cells at 50% confluency in opti-MEM media. The cells were incubated for 4 hours in a humidified, 5% $CO_2$ incubator at 37° C. Then, the media was replaced with Dubelco's modified Eagle Media containing 10% fetal bovine serum, and the cells were incubated for 48 h. The cells were then harvested and the lysate was then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Each complex was tested in duplicate and the mean transfection efficiency was measured in relative light units (RLU).

| Weight ratio polycation to anhydride | Relative Light Units | |
|---|---|---|
| | DM-modification | CDM-modification |
| Polycation DW291 | | |
| 40/0 | | 500 |
| 40/4 | 2,880 | 685 |
| 40/8 | 5,992 | 2,193 |
| 40/16 | 142,977 | 16,468 |
| 40/32 | 1,646,940 | 10,966,755 |
| Polycation DW301 | | |
| 40/4 | 1,375 | 734 |
| 40/8 | 3,874 | 4,510 |
| 40/16 | 129,066 | 41,546 |

-continued

| Weight ratio | Relative Light Units | |
|---|---|---|
| polycation to anhydride | DM-modification | CDM-modification |
| Polycation DW323 | | |
| 40/4 | 13,855 | 4,217 |
| 40/8 | 18,855 | 16,082 |
| 40/16 | 105,980 | 105,107 |

G) In vitro Transfection using pH-labile polyampholytes. Polycation DW297, was modified into a pH-labile polyanion by reaction with a 4 weight excess of CDM aldehyde in the presence of 25-fold weight equivalents HEPES base. DNA (10 µg/mL) in 5 mM HEPES pH 7.5 was condensed by the addition of polycation DW301(10 µg/mL). To the polycation-DNA particle was added the aldehyde-containing, pH-labile polyanion derived from DW297 (30 µg/mL). Particles formulated in this manner are 100–130 nm in size and are stable in 150 mM NaCl. The stability of particle size indicates that a covalent bond between the polycation and the polyanion of the complex has formed via an imine bond. In other words, the aldehyde of the polyanion has formed a bond with polycation, which results in the formation of a polyampholyte. This complex was then added (100 µL) to a well (12-well plates containing 1 mL media) containing mouse hepatoma hepa-1clc7 cells at 50% confluency in opti-MEM media. The cells were incubated for 4 hours in a humidified, 5% $CO_2$ incubator at 37° C. Then, the media was replaced with Dubelco's modified Eagle Media containing 10% fetal bovine serum, and the cells were incubated for 48 h. The cells were then harvested and the lysate was then assayed for luciferase expression as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Each complex was tested in duplicate and the mean transfection efficiency was measured in relative light units (RLU).

| | RLU |
|---|---|
| pH-labile polyampholyte particle | 1,969 |

Example 7

In Vivo Transfections with pH-Labile Polyampholytes

A) Mouse Tail Vein Injections of Complexes of pDNA (pCI Luc)/Silicon Containing Polycations and Polyampholytes.

Several complexes were prepared at a 3:1 charge ratio of polycation to pDNA:

Complex I: pDNA (pCI Luc, 50 µg) in 12.5 mL Ringers
Complex II: pDNA (pCI Luc, 50 µg) was mixed with MC221 in 1.25 mL HEPES 5 mM, pH 7.
This solution was then added to 11.25 mL Ringers.
Complex III: pDNA (pCI Luc, 50 µg) was mixed with MC222 in 1.25 mL HEPES 5 mM, pH 7.
This solution was then added to 11.25 mL Ringers.
Complex IV: pDNA (pCI Luc, 50 µg) was mixed with MC223 in 1.25 mL HEPES 5 mM, pH 7.
This solution was then added to 11.25 mL Ringers.
Complex V: pDNA (pCI Luc, 50 µg) was mixed with MC358 in 1.25 mL HEPES 5 mM, pH 7.
This solution was then added to 11.25 mL Ringers.
Complex VI: pDNA (pCI Luc, 50 µg) was mixed with MC358 and then recharged with SPLL (MC359). This solution was then added to 11.25 mL Ringers.
Complex VII: pDNA (pCI Luc, 50 µg) was mixed with MC360 in 1.25 mL HEPES 5 mM, pH 7.
This solution was then added to 11.25 mL Ringers.
Complex VIII: pDNA (pCI Luc, 50 µg) was mixed with Poly-L-Arginine/-L-Serine(3:1) in 1.25 mL HEPES 5 mM, pH 7. This solution was then added to 11.25 mL Ringers.
Complex IX: pDNA (pCI Luc, 50 µg) was mixed with MC366 and then recharged with SPLL (MC359). This solution was then added to 11.25 mL Ringers.
Complex X: pDNA (pCI Luc, 50 µg) was mixed with MC367 and then recharged with SPLL (MC359). This solution was then added to 11.25 mL Ringers.
Complex XI: pDNA (pCI Luc, 50 µg) was mixed with MC369 and then recharged with SPLL (MC359). This solution was then added to 11.25 mL Ringers.
Complex XII: pDNA (pCI Luc, 50 µg) was mixed with MC370 and then recharged with SPLL (MC359). This solution was then added to 11.25 mL Ringers.

2.5 mL tail vein injections of 2.5 mL of the complex were preformed as previously described. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. The amount of transfection was reported in relative light units and is the average transfection for n separate animals.

| Results: 2.5 mL injections | | |
|---|---|---|
| Complex I: | n = 14 | 14,564,000 RLU |
| Complex II: | n = 14 | 14,264,000 RLU |
| Complex III: | n = 9 | 13,449,000 RLU |
| Complex IV: | n = 3 | 6,927,000 RLU |
| Complex V: | n = 3 | 10,049,000 RLU |
| Complex VI: | n = 3 | 13,879,000 RLU |
| Complex VII: | n = 3 | 10,599,000 RLU |
| Complex VIII: | n = 3 | 638,000 RLU |
| Complex IX: | n = 3 | 12,597,000 RLU |
| Complex X: | n = 3 | 13,093,000 RLU |
| Complex XI: | n = 3 | 25,129,000 RLU |
| Complex XII: | n = 3 | 15,857,000 RLU |

The results indicate that the pDNA is being released from the pDNA/Silicon containing polycation complexes and polyampholyte complexes, and is accessible for transcription. Additionally, the results indicate that complex VIII (does not contain the silicon) is much less effective in the assay than is complex V.

B) In vivo delivery of a pH-labile polyampholyte. Polycation DW297, was modified into a pH-labile polyanion by reaction with 0.05 weight equivalent of CDM-aldehyde followed by a 4-fold weight equivalents of CDM the presence of 25-fold weight equivalent of HEPES base. DNA (50 µg/mL) in 5 mM HEPES pH 7.5 was condensed by the addition of polycation DW301(50 μg/mL). To the polycation-DNA particle was added the aldehyde-containing, pH-labile polyanion derived from DW297 (150 μg/mL). 200 mL of this complex was then injected into the portal vein of ICR mice (20 gm weight on average). After 24 hours, the animals were sacrificed and their livers were assayed for luciferase activity.

| Complex | Relative light units (Average of two animals) |
| --- | --- |
| pH-labile polyampholyte particle | 15,034 |

C) Intravascular delivery of a pH-labile polyampholyte. A pH-labile polyampholyte was synthesized from the polycation PLL by reaction of 30 mg of PLL with 15 mg of CDM, which converts some of the amine groups to carboxylate groups.

To a solution of plasmid DNA pCIluc (10 μg, prepared according to Danko, I., Williams, P., Herweijer, H. Zhang, G., Latendresse, J. S., Bock, I., Wolff, J. A. *Hum. Mol. Genetics* 1997, 6, 1435.) was added polyampholyte as prepared above or the polycation PLL. The amount of PLL added in each sample was 30 μg. These complexes were then added to 2 mL Ringer's solution and injected into the tail vein of ICR mice (20 gm weight on average). After 24 hours, the animals were sacrificed and their livers were assayed for luciferase activity.

| Complex | Relative light units (Average of two animals) |
| --- | --- |
| PLL alone | 67,576 |
| Partial CDM-modified PLL | 144,789 |

Example 8

Kinetic Analysis and PH-Lability Studies

A) Kinetics of conversion of dimethyl maleamic modified poly-L-lysine to poly-L-lysine. Dimethyl maleamic modified poly-L-lysine (10 mg/mL) was incubated in 10 mM sodium acetate buffer pH 5. At various times, aliquots (10 μg) were removed and added to 0.5 mL of 100 mM borax solution containing 0.4 mM trinitrobenzenesulfonate. A half an hour later, the absorbance of the solution at 420 nm was measured. To determine the concentration of amines at each time point, the extinction coefficient was determine for the product of trinitrobenzenesulfonate and poly-L-lysine. Using this extinction coefficient we were able to calculate the amount of amines and maleamic groups at each time point. A plot of ln $(A_t/A_0)$ as a function of time was a straight line whose slope is the negative of the rate constant for the conversion of maleamic acid to amine and anhydride, where $A_t$ is the concentration of maleamic acid at a time t and $A_0$ is the initial concentration of maleamic acid. For two separate experiments we calculated rate constants of 0.066 $sec^{-1}$ and 0.157 $sec^{-1}$ which correspond to half lives of roughly 10 and 4 minutes respectively.

B) Kinetics of conversion of dimethylmaleamic modified $KL_3$ (DM-$KL_3$) to $KL_3$. Dimethyl maleamic modified $KL_3$ (0.1 mg/mL) was incubated in 40 mM sodium acetate buffer pH 5 and 1 mM cetyltrimetylammonium bromide. At various times, aliquots (10 μg) were removed and added to 0.05 mL of 1 M borax solution containing 4 mM trinitrobenzenesulfonate. A half an hour later, the absorbance of the solution at 420 nm was measured. To determine the concentration of amines at each time point, the extinction coefficient was determine for the product of trinitrobenzenesulfonate and poly-L-lysine. Using this extinction coefficient we were able to calculate the amount of amines and maleamic groups at each time point. A plot of ln $(A_t/A_0)$ as a function of time was a straight line whose slope is the negative of the rate constant for the conversion of maleamic acid to amine and anhydride, where $A_t$ is the concentration of maleamic acid at a time t and $A_0$ is the initial concentration of maleamic acid. We calculated a rate constant of 0.087 $sec^{-1}$ that corresponds to a half-life of roughly 8 minutes.

C) Kinetics of hydrolysis of glycolic acid ethoxylate(4 units) 4-tert-buty-1,4-cyclohexadiene. Glycolic acid ethoxylate(4 units) 4-tert-buty-1,4-cyclohexadiene (1 mg) was dissolved in placed into 1 mL of 15 mM sodium acetate pH 5 buffer. The absorbance of the solution at 225 nm, which is the wavelength at which enol ethers absorb (Kresge, A. J.; Sagatys, D. S.; Chen, H. L. *J. Am. Chem. Soc.* 1977, 99, 7228) was measured over time. A fit of the decrease of absorbance as a function of time by an exponential decay function had a rate constant of 0.0159 $min^{-1}$, which corresponds to a half-life of 40 minutes.

D) Kinetics of hydrolysis of poly(oxy-1-para-aceticphenoxymethylethylene-co-oxy-1-methylethylene). Poly(oxy-1-para-aceticphenoxymethylethylene-co-oxy-1-methylethylene) (0.16 mg/mL) was placed into 1 mL of 5 mM sodium acetate buffer pH 5. The absorbance of the solution at 225 nm was measured as a function of time. The amount of time it took for the absorbance to decrease half of maximum was 37 minutes, i.e. the half-life of hydrolysis is 37 minutes.

E) Particle Formation of poly(oxy-1-para-aceticphenoxymethylethylene-co-oxy-1-methylethylene) as a Function of Acidification and Time. To a solution (0.5 mL) of 5 mM HEPES pH 8 was added poly(oxy-1-para-aceticphenoxymethylethylene-co-oxy-1-methylethylene) (54 μg/mL) which had been incubated for various times in the presence of 1 mM acetic acid (pH4–5), followed by the addition of polyallylamine. The intensity of the scattered light and the size of the particle were measured (using a Brookhaven ZetaPlus Particle Sizer) as a function of the amount of time the polymer was incubated under acidic conditions.

| Time at pH 4–5 (minutes) | Size (nm) | Scattered light intensity (kilocounts per second) |
| --- | --- | --- |
| 0 | 231 | 390 |
| 1 | 195 | 474 |
| 2 | 208 | 460 |
| 5 | 224 | 450 |
| 15 | 124 | 92 |
| 39 | 132 | 250 |

F) Kinetics of Cleavage of Ketal

F-1) Esterification of Carboxylic Acid Modified Microspheres with Di-(2-methyl-4-hydroxymethyl-1,3-dioxolane)-1,4-benzene. To a suspension of carboxylic acid modified microspheres (1000 μL, 2% solids, Molecular Probes) in $H_2O$ (500 μL) was added 1-(3-dimethylaminopropyl)-3-ethylcarbodiimide hydrochloride (7.0 mg, 36 μmol, Aldrich Chemical Company), followed by di-(2-methyl-4-hydroxymethyl-1,3-dioxolane)-1,4-benzene (23 mg, 73 μmol), and the suspension was stirred at room temperature. After 16 hrs, the microspheres were removed by centrifugation. The supernatant was removed and the pellet was resuspended in 1.5 mL H$_2$O to wash. The microspheres were washed an additional 2×1.5 mL H$_2$O and suspended in 1 mL H$_2$O.

F-2) Aldehyde Derivatization of Esterified Carboxylic Acid Modified Microspheres with Di-(2-methyl-4-hydroxymethyl-1,3-dioxolane)-1,4-benzene. To a solution of succinic semialdehyde (3.7 mg, 36 µmol, Aldrich Chemical Company) in H$_2$O was added 1-(3-dimethylaminopropyl)-3-ethylcarbodiimide hydrochloride (8.7 mg, 46 µmol, Aldrich Chemical Company) followed by N-hydroxysuccinimide (5.3 mg, 46 µmol, Aldrich Chemical Company). The solution was stirred for 20 min at which time carboxylic acid modified microspheres esterified with di-(2-methyl-4-hydroxymethyl-1,3-dioxolane)-1,4-benzene (500 µL) were added. After 16 hrs, the microspheres were removed by centrifugation. The supernatant was removed and the pellet was resuspended in 1 mL H$_2$O to wash. The microspheres were washed an additional 2×1 mL H$_2$O and suspended in 1 mL H$_2$O. The aldehyde content of the microspheres was determined on a 50 µL sample of the suspension with 2,4-dinitrophenylhydrazine and NaBH$_3$CN. The absorbance measured at 349 nm and fitted against a standard curve indicated 18 µmol of aldehyde present in the reaction sample.

Attachment of Membrane Active Peptide to Acid Labile Moieties and Lability Studies of these Systems:

F-3) Attachment of a Peptide (Melittin) to the Aldehyde Derivedfrom Carboxylic Acid Modified Microspheres Esterified with Di-(2-methyl-4-hydroxymethyl-1,3-dioxolane)-1,4-benzene. To 100 µL of the aldehyde derivatized microshpere suspension was added 400 µL H$_2$O and melittin (1 mg, 0.4 µmol, Mirus Corporation). After 12 hrs, NaBH$_3$CN (0.6 mg, 9 µmol, Aldrich Chemical Company) was added. After 1 hr, the suspension was centrifugated to pellatize the microspheres. The supernatant was removed and the pellet was resuspended in 1 mL H$_2$O to wash. The microspheres were washed an additional 3×1 mL H$_2$O and suspended in 1 mL H$_2$O. The last wash indicated the presence of active peptide based on red blood cell lysis activity. The sample was washed 1×25 mM HEPES, and 1×H$_2$O. The final wash was free of peptide based on red blood cell lysis assay.

F-4) Blood Lysis Experiment on Melittin Conjugated to Microspheres via the Di-(2-methyl-4-hydroxymethyl-1,3-dioxolane)-1,4-benzene. The microspheres were taken up in H$_2$O (500 µL) and partitioned into five 100 µL samples. Four of the samples were diluted to 1000 µL with sodium phosphate buffer (100 mM) at pH 7.5, 6.0, 5.5, and 5.0. Samples were held at 37° C., spun down, and 150 µL aliquots taken at 30 min, 60 min, 90 min, and 16 hrs. A portion of each sample (100 µL) was diluted with sodium phosphate buffer (400 µL, pH 7.5) and added to red blood cells (100 µL, pH 7.5). Red blood cell lysis was measured after 10 min by measuring the absorbance at 541 nm.

A control sample was also measured in which 100% of the red blood cells had been lysed with melittin alone.

| Sample | A$_{541}$ |
|---|---|
| Blood | 0.026 |
| 100% lysis | 1.881 |
| 30 min pH 7.5 | 0.026 |

-continued

| Sample | A$_{541}$ |
|---|---|
| 30 min pH 6.0 | 0.326 |
| 30 min pH 5.5 | 0.609 |
| 30 min pH 5.0 | 0.659 |
| 60 min pH 7.5 | 0.027 |
| 60 min pH 6.0 | 0.212 |
| 60 min pH 5.5 | 0.526 |
| 60 min pH 5.0 | 0.730 |
| 90 min pH 7.5 | 0.036 |
| 90 min pH 6.0 | 0.390 |
| 90 min pH 5.5 | 0.640 |
| 90 min pH 5.0 | 0.892 |
| 16 hrs pH 7.5 | 0.065 |
| 16 hrs pH 6.0 | 0.354 |
| 16 hrs pH 5.5 | 0.796 |
| 16 hrs pH 5.0 | 1.163 |

The fifth 100 µL sample was further divided into 25 µL samples, three of which were diluted to 250 µL with sodium phosphate buffer (100 mM) at pH 7.5, 6.0, and 5.0. The samples were held at 37° C. for 30 min, spun down and the supernatant removed, and resuspended in 2.5 M NaCl solution (50 µL) and mixed. After 10 min the microspheres were spun down and the supernatant removed. The samples were added to red blood cells (500 µL, 100 mM) and the absorbance was measured at 541 nm.

| Sample | A$_{541}$ |
|---|---|
| Blood (NaCl wash) | 0.041 |
| pH 7.5 | 0.053 |
| pH 7.5 (NaCl wash) | 0.087 |
| pH 6.0 | 0.213 |
| pH 6.0 (NaCl wash) | 0.162 |
| pH 5.0 | 0.685 |
| pH 5.0 (NaCl wash) | 0.101 |

The results indicate that under acidic conditions, the modified peptide is released from the microsphere and is available to interact with the cell membrane as indicated by the red blood cell lysis. The results indicate that the modified peptide is not released at pH 7.5. Additionally, the lysis activity results indicate the release of modified peptide is rapid at all acidic pH levels tested (t<30 min) with slow continual release thereafter, and that more modified peptide is released at lower pH (larger red blood cell lysis). The results also indicate that more modified peptide is released upon washing the microsphere with a salt solution.

F-5) Attachment of a Peptide (Melittin) to the Aldehyde Derivedfrom Poly-Glutamic Acid Partially Esterified with Di-(2-methyl-4-hydroxymethyl-1,3-dioxolane)-1,4-benzene. To a solution of the aldehyde-poly-glutamic acid compound (1.0 mg, 7.7 µmol) in water (200 µL) was added melittin (4.0 mg, 1.4 µmol) and the reaction mixture was stirred at room temperature. After 12 hrs the reaction mixture was divided into two equal portions. One sample (100 µL) was dialyzed against 1% ethanol in water (2×1 L, 12,000–14,000 MWCO) and tested utilizing a theoretical yield of 1.7 mg. To the second portion (100 µL) was added sodium cyanoborohydride (1.0 mg, 16 µmol, Aldrich Chemical Company). The solution was stirred at room temperature for 1 hr and then dialyzed against water (2×1 L, 12,000–14,000 MWCO). The resulting material was utilized assuming a theoretical yield of 1.7 mg of conjugate.

Lability of Polymers Containing Acid Labile Moieties:

F-6) Particle Sizing and Acid Lability of Poly-L-Lysine/Ketal Acid of Polyvinylphenyl Ketone and Glycerol Ketal Complexes. Particle sizing (Brookhaven Instruments Corporation, ZetaPlus Particle Sizer, I90, 532 nm) indicated an effective diameter of 172 nm (40 µg) for the ketal acid. Addition of acetic acid to a pH of 5 followed by particle sizing indicated a increase in particle size to 84000 nm.

A poly-L-lysine/ketal acid (40 µg, 1:3 charge ratio) sample indicated a particle size of 142 nm. Addition of acetic acid (5 µL, 6 N) followed by mixing and particle sizing indicated an effective diameter of 1970 nm. This solution was heated at 40° C. Particle sizing (by a Brookhaven ZetaPlus Particle Sizer) indicated an effective diameter of 74000 nm and a decrease in particle counts.

Results: The particle sizer data indicates the loss of particles upon the addition of acetic acid to the mixture.

F-7) Particle Sizing and Acid Lability of Poly-L-Lysine/Ketalfrom Polyvinyl Alcohol and 4-Acetylbutyric Acid Complexes. Particle sizing (Brookhaven Instruments Coporation, ZetaPlus Particle Sizer, I90, 532 nm) indicated an effective diameter of 280 nm (743 kcps) for poly-L-lysine/ketal from polyvinyl alcohol and 4-acetylbutyric acid complexes (1:3 charge ratio). A poly-L-lysine sample indicated no particle formation. Similarly, a ketal from polyvinyl alcohol and 4-acetylbutyric acid sample indicated no particle formation.

Acetic acid was added to the poly-L-lysine/ketal from polyvinyl alcohol and 4-acetylbutyric acid complex to a pH of 4.5. Particle sizing (by a Brookhaven ZetaPlus Particle Sizer) indicated particles of 100 nm, but at a low count rate (9.2 kcps). Results: The particle size data indicates the loss of particles upon the addition of acetic acid to the mixture.

F-8) Size Exclusion Chromatography and Acid Lability of MC228. MC208 (1.5 mg) was taken up in 50 mM HEPES (0.3 mL, pH 8.5) and passed through a Sephadex G50 column (8 cm column, 50 mM HEPES (pH 8.5) eluent) and 0.5 mL fractions were collected. The absorbance of the fractions was determined at 300 nm. Two additional samples (1.5 mg) were prepared in 50 mM Citrate buffer at pH 2 and pH 5 (0.3 mL) and allowed to sit a room temperature for 45 min prior to running on the Sephadex G50 column (8 cm column, 50 mM HEPES (pH 8.5) eluent). The absorbance of the fractions was determined at 300 nm.

| Fraction number | pH 8.5 | pH 5 | pH 2 |
|---|---|---|---|
| 1 | 0.018 | 0.040 | 0.022 |
| 2 | 0.024 | 0.019 | 0.013 |
| 3 | 0.019 | 0.015 | 0.008 |
| 4 | 0.028 | 0.118 | 0.024 |
| 5 | 0.287 | 0.527 | 0.293 |
| 6 | 1.091 | 0.693 | 0.604 |
| 7 | 0.976 | 0.818 | 0.715 |
| 8 | 0.888 | 1.071 | 0.895 |
| 9 | 0.907 | 1.178 | 1.082 |
| 10 | 0.944 | 1.289 | 1.298 |
| 11 | 0.972 | 1.296 | 1.423 |
| 12 | 0.941 | 1.212 | 1.326 |
| 13 | 0.913 | 0.924 | 1.140 |
| 14 | 0.764 | 0.640 | 1.012 |
| 15 | 0.589 | 0.457 | 0.841 |
| 16 | 0.415 | 0.264 | 0.655 |

Results: The column demonstrates that upon incubating the sample under acidic conditions, the molecular weight of the polymer is decreased indicating the polymer is labile under acidic conditions.

F-9) Acid Lability of MC208. A sample of MC208 in dimethylformamide (20 µL) was divided into four equal samples. To each sample was added citrate buffer (100 µL, pH 4) and the resulting samples (final pH of 5) were incubated at 37° C. for 2, 4, 8, and 24 hrs. The samples were then analyzed by thin layer chromatography against a sample not exposed to acidic conditions. The results indicated increasing amounts of higher Rf material with increasing time, indicated degradation of the polymer.

F-10) Particle Sizing and Acid Lability of pDNA (pCI Luc)/MC208 Complexes. Particle sizing (Brookhaven Instruments Coporation, ZetaPlus Particle Sizer, I90, 532 nm) indicated an effective diameter of 293 nm (687 kcps) for pDNA (25 µg pDNA)/di-(2-methyl-4-hydroxymethyl(succinic semialdehyde ester)-1,3-dioxolane)-1,4-benzene: 1,4-bis(3-aminopropyl)-piperazine copolymer complexes (1:3 charge ratio). HCl was added to the complex to approximately pH 5 and the particle size was measured. The reading indicated particles with an effective diameter of 11349 nm (120 kcps).

Results: The particle size data indicates MC208 compacts pDNA into small particles. The results also indicate the loss of particles upon the addition of HCl to the mixture by flocculation.

G) Kinetics of Cleavage of Imine. Particle Sizing and Acid Lability of pDNA (pCI Luc)/1,4-Bis(3-aminopropyl)piperazine Glutaric Dialdehyde Copolymer Complexes. To 50 µg pDNA in 2 mL HEPES (25 mM, pH 7.8) was added 135 µg 1,4-bis(3-aminopropyl)piperazine glutaric dialdehyde copolymer. Particle sizing (Brookhaven Instruments Coporation, ZetaPlus Particle Sizer, I90, 532 nm) indicated an effective diameter of 110 nm for the complex. A 50 µg pDNA in 2 mL HEPES (25 mM, pH 7.8) sample indicated no particle formation. Similarly, a 135 µg 1,4-bis(3-aminopropyl)piperazine glutaric dialdehyde copolymer in 2 mL HEPES (25 mM, pH 7.8) sample indicated no particle formation. Acetic acid was added to the pDNA (pCI Luc)/1,4-bis(3-aminopropyl)piperazine glutaric dialdehyde copolymer complex to a pH of 4.5. Particle sizing indicated particles of 2888 nm, and aggregation was observed.

Results: 1,4-Bis(3-aminopropyl)piperazine-glutaric dialdehyde copolymer condenses pDNA, forming small particles. Upon acidification, the particle size increases, and aggregation occurs, indicating cleavage of the polymeric imine.

Example 9

Hemolysis Assay

A) Lysis of Erythrocytes by the peptides Melittin and $KL_3$ and their dimethylmaleamic acid derivatives as a function of pH. The membrane-disruptive activity of the peptide melittin and subsequent blocking of activity by anionic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 uL of this suspension was used for each tube. This yields $10^8$ RBCs per tube. Each tube contained 800 uL of buffer, 200 uL of the RBC suspension, and the peptide with or without polymer. Each sample was then repeated to verify reproducibility. The tubes were incubated for 30 minutes in a 37° C. water bath. They were spun for 5 min at full speed in the microcentifuge. Lysis was determined by measuring the absorbance of the supernatant at 541 nm, reflecting the amount of hemoglobin that had been released into the supernatant. Percent hemolysis was calculated assuming 100% lysis to be measured by the hemoglobin released by the red blood cells in water; controls of RBCs in buffer with no peptide were also run.

| Peptide | Percent Hemolysis | |
|---|---|---|
| | pH 5.4 | pH 7.5 |
| Unmodified Peptides | | |
| $KL_3$ | 86, 77, 86 | 54, 77, 54 |
| Melittin | 85 | 92 |
| Dimethylmaleamic Derivatives | | |
| $KL_3$ | 30, 55, 26 | 8, 3, 2 |
| Melittin | 100 | 1 |
| Succinyl Derivatives | | |
| $KL_3$ | 2, 2, 2 | 1, 1, 2 |
| Melittin | 5 | 2 |

B) Lysis of Erythrocytes by Poly Propacrylic Acid and subsequent blocking of activity by cationic polymers with reversible blocking of activity with cleavable disulfide cations in the presence of Glutathione. The pH-dependent membrane-disruptive activity of the PPAAc and subsequent blocking of activity by cationic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 L of this suspension was used for each tube. This yields $10^8$ RBCs per tube. Each tube contained 800 L of buffer, 200 L of the RBC suspension, and the polymer. Each sample was done in triplicate, and was then repeated to verify reproducibility. The tubes were incubated for an hour and a half in a 37° C. water bath. They were spun for 5 min at full speed in the microcentifuge. Lysis was determined by measuring the absorbance of the supernatant at 541 nm, reflecting the amount of hemoglobin which had been released into the supernatant. Percent hemolysis was calculated assuming 100% lysis to be measured by the hemoglobin released by the red blood cells in water; controls of RBCs in buffer with no polymer were also run.

| Results at pH 6.0: | |
|---|---|
| Mock: | 3% |
| PPAAc: | 98% |
| PPAAc + p-L-Lysine | 3% |
| PPAAc + p-L-Lysine w/1 mM Glutathione | 2% |
| PPAAc + 5,5'-Dithiobis(2-nitrobenzoic acid)-1,4-Bis(3-aminopropyl)piperazine Copolymer | 12% |
| PPAAc + 5,5'-Dithiobis(2-nitrobenzoic acid)-1,4-Bis(3-aminopropyl)piperazine Copolymer w/1 mM Glutathione | 98% |
| PPAAc + L-cystine-1,4-bis(3-aminopropyl)piperazine copolymer | 2% |
| PPAAc + L-cystine-1,4-bis(3-aminopropyl)piperazine copolymer w/1 mM Glutathione | 20% |

C) Lysis of Erythrocytes by the peptide Melittin or KL3 and subsequent blocking of activity by anionic polymers or modification with dimethylmaleic anhydride. The membrane-disruptive activity of the peptide melittin and subsequent blocking of activity by anionic polymers was measured using a red blood cell (RBC) hemolysis assay. RBCs were harvested by centrifuging whole blood for 4 min. They were washed three times with 100 mM dibasic sodium phosphate at the desired pH, and resuspended in the same buffer to yield the initial volume. They were diluted 10 times in the same buffer, and 200 uL of this suspension was used for each tube. This yields $10^8$ RBCs per tube. Each tube contained 800 uL of buffer, 200 uL of the RBC suspension, and the peptide with or without polymer. Each sample was then repeated to verify reproducibility. The tubes were incubated for 30 minutes in a 37° C. water bath. They were spun for 5 min at full speed in the microcentifuge. Lysis was determined by measuring the absorbance of the supernatant at 541 nm, reflecting the amount of hemoglobin that had been released into the supernatant. Percent hemolysis was calculated assuming 100% lysis to be measured by the hemoglobin released by the red blood cells in water; controls of RBCs in buffer with no peptide were also run.

| Results at pH 7.5: | |
|---|---|
| Mock: | 1% |
| Melittin | 100% |
| Melittin + pAcrylic Acid | 9% |
| DM-Melittin | 1% |
| DM-Melittin post incubation at pH4 30 seconds | 100% |
| KL3 | 86% |
| DM-KL3 | 4% |
| DM-KL3 post incubation at pH 5.4 30 seconds | 85% |

Example 10

Endosome Lysis. Endosome Disruption Assay with Dimethylmaleamic-modified melittin. HeLa cells were plated in 6-well tissue culture dishes containing microscope slide coverslips and grown in Delbecco's Modified Eagle's Medium (DMEM)+10% fetal calf serum+penn/strep for 24–48 hours until 30–60% confluent. Growth media was aspirated and 1 ml pre-heated (37° C.) serum-free DMEM+2 mg/ml fluorescein isothiocyanate (FITC) labeled dextran(10 kDa)±50 μg DM-melittin or 50 μg melittin was added to the cells and incubated at 37° C. in a humidified $CO_2$ incubator. After 25 min, media containing FITC-dextran±melittin was removed, the cells were washed twice with 1 ml 37° C. DMEM lacking FITC-dextran and melittin, and cells were incubated for an additional 35 min at 37° C. in 1 ml fresh DMEM. In order to assess possible cell lysis caused by melittin, propidium iodide was added for the final 5 min of incubation. Propidium iodide is impermeable to the cell plasma membrane and thus does not stain live cells. However, if the plasma membrane has been damaged, propidium iodide enters the cell where it will brightly stain the nucleus. To process slides for analysis, cells were washed 3 times with cold phosphate buffered saline (PBS), fixed in PBS+4% formaldehyde for 20–30 min at 4° C., and washed again 3 times with cold PBS. Excess liquid was drained from coverslips which were then mounted onto glass slides. Fluorescence was then analyzed on a Zeiss LSM510 confocal microscope. FITC was excited by a 488 nm argon laser and fluorescence emission was detected by a long pass 505 nm filter. FITC-dextran that had been internalized but not released from internal vesicles/endosomes appeared as a punctate cytoplasmic signal. In the presence of DM-melittin, a loss of punctate cytoplasmic signal was observed with a concomitant appearance of a diffuse cytoplasmic signal, indicative of release of dextran from endosomes. For cells incubated with unmodified melittin near 100% cell death was observed as determined by propidium iodide staining of nuclei and loss of cells from the sample.

Example 11

In Vivo Circulation Studies. General procedure for the reaction of poly-L-Lysine compacted DNA particles polyethylene glycol methyl ether 2-propionic-3-methylmaleate (CDM-PEG). Plasmid DNA (200 µg/ml) in 290 mM Glucose/5 mM Hepes pH8 was compacted with poly-L-Lysine (mw: 52,000) (144 µg/ml). This particle is then reacted with 0.5, 1, 2 or 5-fold weight excess of CDM-PEG to amines on the poly-L-lysine.

Effect of CDM-PEG modified poly-L-lysine:DNA particles in vivo. Plasmid DNA labeled with Cy3 Label IT(Mirus Corporation, Madison, Wis.) was compacted into a particle with a 1.2 fold charge excess of poly-L-lysine (mw: 52,000). The particles were then reacted with either a non-reactive Polyethylene Glycol (mw: 5000) or with amine-reactive CDM-PEG at a 0.5 molar equivalent to amines on the poly-L-lysine. 50 µg aliquots of DNA were injected into the tail vein of male ICR mice of approximately 20 grams in weight. Blood was taken at one hour and the smears were inspected for Cy3 fluorescence still in circulation. The animals were then sacrificed and the liver, lung, kidney and spleen were harvested and snap frozen for cryosectioning and the resulting slices were inspected for Cy3 fluorescence.

Results: The animal injected with the fluorescent particles treated with non-reactive Polyethylene Glycol showed no fluorescence in circulation in the blood at one hour and very little fluorescence in the liver, kidney or spleen, leaving the significant portion of fluorescence in the lung. The animal injected with the fluorescent particles treated with CDM-PEG showed a high level of fluorescence still in circulation in the blood at one hour and also had a high level of fluorescence evenly spread throughout the liver, some spread in the kidney and spleen, with little fluorescence in the lung.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Various modifications of the described modes for carrying out the invention which are obvious to those skilled in cell biology, chemistry, molecular biology, biochemistry or related fields are intended to be within the scope of the following claims.

We claim:

1. A process for delivering a nucleic acid to a cell comprising:
   a) condensing a nucleic acid with a polyampholyte to form a complex;
   b) crosslinking the polyampholyte; and,
   c) contacting the cell with the crosslinked complex.

2. The process of claim 1 wherein the nucleic acid consists essentially of RNA.

3. The process of claim 1 wherein the nucleic acid consists of an oligonucleotide.

4. The process of claim 1 wherein the crosslinked complex is less in 100 nm in size.

5. The process of claim 1 wherein the nucleic acid consists of DNA.

6. The process of claim 5 wherein the DNA contains an expressible sequence.

7. The process of claim 1 wherein the polyampholyte consists of a labile polyampholyte.

8. The process of claim 7 wherein the polyampholyte consists of a pH labile polyampholyte.

9. The process of claim 8 wherein the polyampholyte contains at least one pH labile bond in which the half-life of the pH labile bond is less than 45 minutes at pH 5.

10. The process of claim 8 wherein the polyampholyte contains at least one pH labile bond in which the half-life of the pH labile bond is less than 15 minutes at pH 5.

11. A particle for delivering a nucleic acid to a cell formed by the process comprising:
   a) condensing a nucleic acid with a polycation to form a complex;
   b) adding a polyanion to the complex to form a tertiary complex; and
   c) crosslinking the polyanion to the polycation to form a particle.

12. The particle of claim 11 wherein the polycation contains a labile bond.

13. The particle of claim 11 wherein the polyanion contains a labile bond.

14. The particle of claim 11 wherein crosslinking the polyanion to the polycation forms a multivalent block polyampholyte.

15. The particle of claim 11 wherein the polyanion is crosslinked to the polycation via a labile bond.

16. The particle of claim 11 wherein crosslinking the polyanion to the polycation comprises adding a crosslinker to the tertiary complex.

17. The particle of claim 16 wherein the crosslinker contains a labile bond.

18. The particle of claim 11 wherein the nucleic acid consists essentially of RNA.

19. The particle of claim 11 wherein the nucleic acid consists of an oligonucleotide.

20. The particle of claim 11 wherein the nucleic acid consists of DNA.

21. The particle of claim 20 wherein the DNA contains an expressible sequence.

22. A process for delivering a nucleic acid to a cell comprising:
   a) condensing a nucleic acid with a polycation to form a complex,
   b) adding a polyanion to the complex to form a tertiary complex,
   c) crosslinking the polyanion to the polycation to form a particle; and,
   d) contacting the cell with the particle.

23. The process of claim 22 wherein the polycation contains a labile bond.

24. The process of claim 22 wherein the polyanion contains a labile bond.

25. The process of claim 22 wherein crosslinking the polyanion to the polycation forms a multivalent block polyampholyte.

26. The process of claim 22 wherein the polyanion is crosslinked to the polycation via a labile bond.

27. The process of claim 22 wherein crosslinking the polyanion to the polycation comprises adding a crosslinker to the tertiary complex.

28. The process of claim 27 wherein the crosslinker contains a labile bond.

29. The process of claim 22 wherein the nucleic acid consists essentially of RNA.

30. The process of claim 22 wherein the nucleic acid consists of an oligonucleotide.

31. The process of claim 22 wherein the nucleic acid consists of DNA.

32. The process of claim 31 wherein the DNA contains an expressible sequence.

* * * * *